(12) United States Patent
Glutz et al.

(10) Patent No.: US 10,433,863 B2
(45) Date of Patent: Oct. 8, 2019

(54) ULTRASONIC SURGICAL INSTRUMENT WITH BLADE COOLING THROUGH RETRACTION

(71) Applicant: Ethicon Endo-Surgery, Inc., Cincinnati, OH (US)

(72) Inventors: Lukas Glutz, Bern (CH); Joël Fontannaz, Bulle (CH); Amir Feriani, Auvernier (CH); Emmanuel Gremion, Echarlens (CH)

(73) Assignee: Ethicon LLC, Guaynabo, PR (US)

( * ) Notice: Subject to any disclaimer, the term of this patent is extended or adjusted under 35 U.S.C. 154(b) by 829 days.

(21) Appl. No.: 14/553,378

(22) Filed: Nov. 25, 2014

(65) Prior Publication Data

US 2016/0143659 A1      May 26, 2016

(51) Int. Cl.
*A61B 17/32* (2006.01)
*A61B 18/00* (2006.01)

(52) U.S. Cl.
CPC ......... *A61B 17/320092* (2013.01); *A61B 17/320068* (2013.01); *A61B 2017/320084* (2013.01);

(Continued)

(58) Field of Classification Search
CPC .... A61B 17/320092; A61B 17/320068; A61B 2017/320084; A61B 2018/0063; A61B 2018/00011
See application file for complete search history.

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| CN | 101674780 A | 3/2010 |
| GB | 2 176 110 A | 12/1986 |

(Continued)

OTHER PUBLICATIONS

U.S. Appl. No. 14/552,530.

(Continued)

*Primary Examiner* — Anh T Dang
(74) *Attorney, Agent, or Firm* — Frost Brown Todd LLC

(57) ABSTRACT

A surgical apparatus comprises a body, a shaft assembly, an end effector, and a blade cooling system. The shaft assembly couples the end effector and the body together. The shaft assembly comprises an acoustic waveguide and defines an interior space. The acoustic waveguide is configured to couple with an ultrasonic transducer. The end effector comprises a clamp arm and an ultrasonic blade in acoustic communication with the ultrasonic transducer. The clamp arm is configured to pivot toward and away from the ultrasonic blade. The shaft assembly comprises an inner tube configured to longitudinally translate to thereby pivot the clamp arm toward and away from the ultrasonic blade. The cooling system is operable to deliver liquid coolant a distal portion of the shaft. A trigger of the body is operable to rotate to thereby translate the ultrasonic blade into and out of the interior space of the shaft assembly to thereby cool the ultrasonic blade.

20 Claims, 26 Drawing Sheets

(52) U.S. Cl.
CPC .............. *A61B 2018/00011* (2013.01); *A61B 2018/0063* (2013.01)

(56) References Cited

U.S. PATENT DOCUMENTS

| | | | |
|---|---|---|---|
| 5,873,873 A | 2/1999 | Smith et al. | |
| 5,980,510 A | 11/1999 | Tsonton et al. | |
| 6,056,735 A | 5/2000 | Okada et al. | |
| 6,193,709 B1 | 2/2001 | Miyawaki et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,358,267 B1 | 3/2002 | Murakami et al. | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,066,936 B2 | 6/2006 | Ryan | |
| 7,074,219 B2 | 7/2006 | Levine et al. | |
| 7,235,073 B2 | 6/2007 | Levine et al. | |
| 7,563,269 B2 | 7/2009 | Hashiguchi | |
| 8,057,498 B2 | 11/2011 | Robertson | |
| 8,328,834 B2 | 12/2012 | Isaacs et al. | |
| 8,348,880 B2 | 1/2013 | Messerly et al. | |
| 8,444,663 B2 | 5/2013 | Houser et al. | |
| 8,461,744 B2 | 6/2013 | Wiener et al. | |
| 8,591,459 B2 | 11/2013 | Clymer et al. | |
| 8,591,536 B2 | 11/2013 | Robertson | |
| 8,623,027 B2 | 1/2014 | Price et al. | |
| 8,652,132 B2 | 2/2014 | Tsuchiya et al. | |
| 8,662,745 B2 | 3/2014 | Mishuchenko et al. | |
| 8,685,020 B2 | 4/2014 | Weizman et al. | |
| 8,911,460 B2 | 12/2014 | Neurohr et al. | |
| 8,974,447 B2 | 3/2015 | Kimball et al. | |
| 8,986,302 B2 | 3/2015 | Aldridge et al. | |
| 9,005,199 B2 | 4/2015 | Beckman et al. | |
| 9,023,071 B2 | 5/2015 | Miller et al. | |
| 2006/0079874 A1 | 4/2006 | Faller et al. | |
| 2006/0265035 A1* | 11/2006 | Yachi | A61B 17/320092 607/101 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0036914 A1 | 2/2009 | Houser | |
| 2009/0143795 A1* | 6/2009 | Robertson | A61B 17/320092 606/169 |
| 2010/0331873 A1 | 12/2010 | Dannaher et al. | |
| 2012/0112687 A1 | 5/2012 | Houser et al. | |
| 2012/0116265 A1 | 5/2012 | Houser et al. | |
| 2013/0303949 A1 | 11/2013 | Kawaguchi et al. | |
| 2014/0005668 A1 | 1/2014 | Rhee et al. | |
| 2014/0005701 A1 | 1/2014 | Olson et al. | |
| 2014/0005704 A1* | 1/2014 | Vakharia | A61B 17/320092 606/169 |
| 2014/0012297 A1 | 1/2014 | Ross et al. | |
| 2014/0012298 A1 | 1/2014 | Cunningham et al. | |
| 2014/0012299 A1 | 1/2014 | Stoddard et al. | |
| 2014/0114334 A1 | 4/2014 | Olson et al. | |
| 2014/0135804 A1 | 5/2014 | Weisenburgh et al. | |
| 2014/0163549 A1 | 6/2014 | Yates et al. | |
| 2014/0180002 A1 | 6/2014 | Voic | |
| 2014/0330298 A1 | 11/2014 | Arshonsky et al. | |
| 2015/0080925 A1 | 3/2015 | Schulte et al. | |
| 2015/0148832 A1 | 5/2015 | Boudreaux et al. | |
| 2015/0148833 A1 | 5/2015 | Stokes et al. | |
| 2015/0148834 A1 | 5/2015 | Gee et al. | |
| 2015/0148835 A1 | 5/2015 | Faller et al. | |

FOREIGN PATENT DOCUMENTS

| | | |
|---|---|---|
| JP | 2001-353165 A | 12/2001 |
| JP | 2014-000311 | 1/2014 |
| WO | WO 2012/116957 | 9/2012 |
| WO | WO 2013/183715 | 12/2013 |
| WO | WO 2013/190937 A1 | 12/2013 |
| WO | WO 2013/062103 | 4/2015 |

OTHER PUBLICATIONS

U.S. Appl. No. 14/552,552.
U.S. Appl. No. 14/552,614.
U.S. Appl. No. 14/552,681.
International Search Report and Written Opinion dated Feb. 22, 2016 for Application No. PCT/US2015/061561, 11 pgs.
U.S. Appl. No. 61/410,603, filed Nov. 5, 2010.
U.S. Appl. No. 61/908,920, filed Nov. 26, 2013.
U.S. Appl. No. 14/553,142, filed Nov. 25, 2014.
U.S. Appl. No. 14/553,329, filed Nov. 25, 2014.
U.S. Appl. No. 14/553,378, filed Nov. 25, 2014.
Chinese Office Action, The First Office Action, and First Search Report dated Apr. 2, 2019 for Application No. CN 201580063731.3, 12 pgs.
European Examination Report dated Feb. 21, 2019 for Application No. EP 15813160.7, 4 pgs.

* cited by examiner

ULTRASONIC SURGICAL INSTRUMENT WITH BLADE COOLING THROUGH RETRACTION

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015 the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
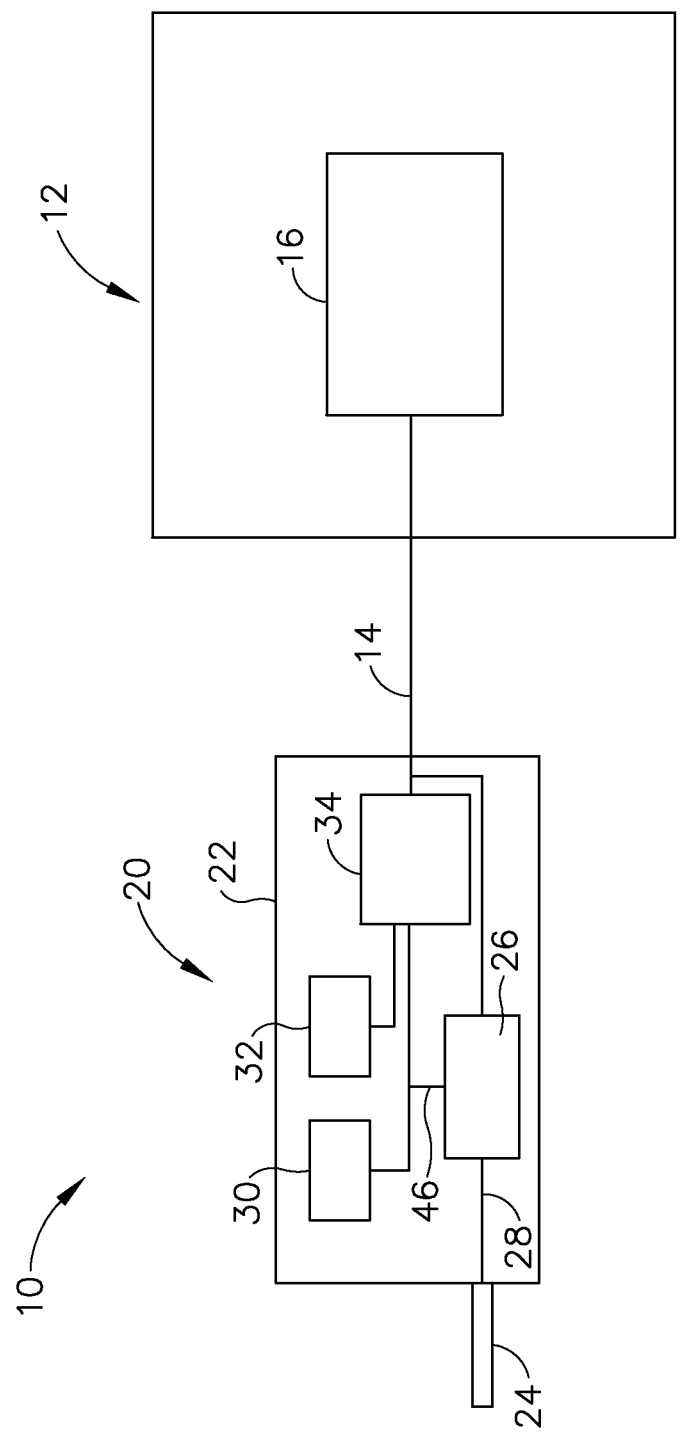
FIG. 1 depicts a block schematic view of an exemplary surgical system.
Figure 2:
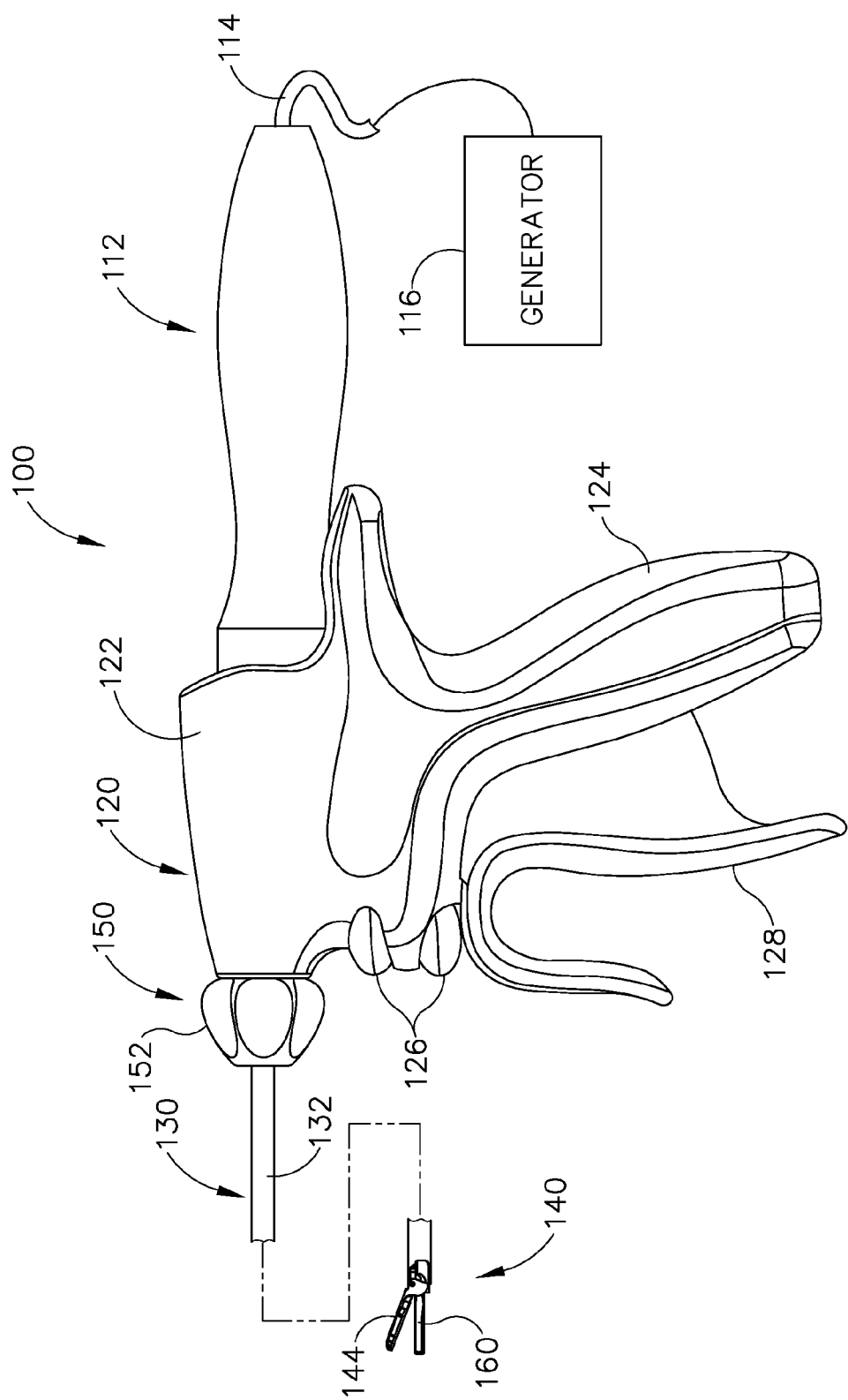
FIG. 2 depicts a side elevational view of an exemplary surgical instrument operable for use with the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of instrument (100) may be constructed and operable in accordance with at least some of the teachings of U.S. Pat. Nos. 5,322,055; 5,873,873; 5,980, 510; 6,325,811; 6,773,444; 6,783,524; 8,461,744; 8,623, 027; U.S. Pub. No. 2006/0079874, now abandoned; U.S. Pub. No. 2007/0191713, now abandoned; U.S. Pub. No. 2007/0282333, now abandoned; U.S. Pub. No. 2008/ 0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028, 717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a handle (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with handle (128) such that clamp arm (144) is pivotable toward ultrasonic blade (160) in response to pivoting of handle (128) toward pistol grip (124); and such that clamp arm (144) is pivotable away from ultrasonic blade (160) in response to pivoting of handle (128) away from pistol grip (124). Various suitable ways in which clamp arm (144) may be coupled with handle (128) will be apparent to those of ordinary skill in the art in view of the teachings herein. In some versions, one or more resilient members are used to bias clamp arm (144) and/or handle (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about handle (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

Figure 3:
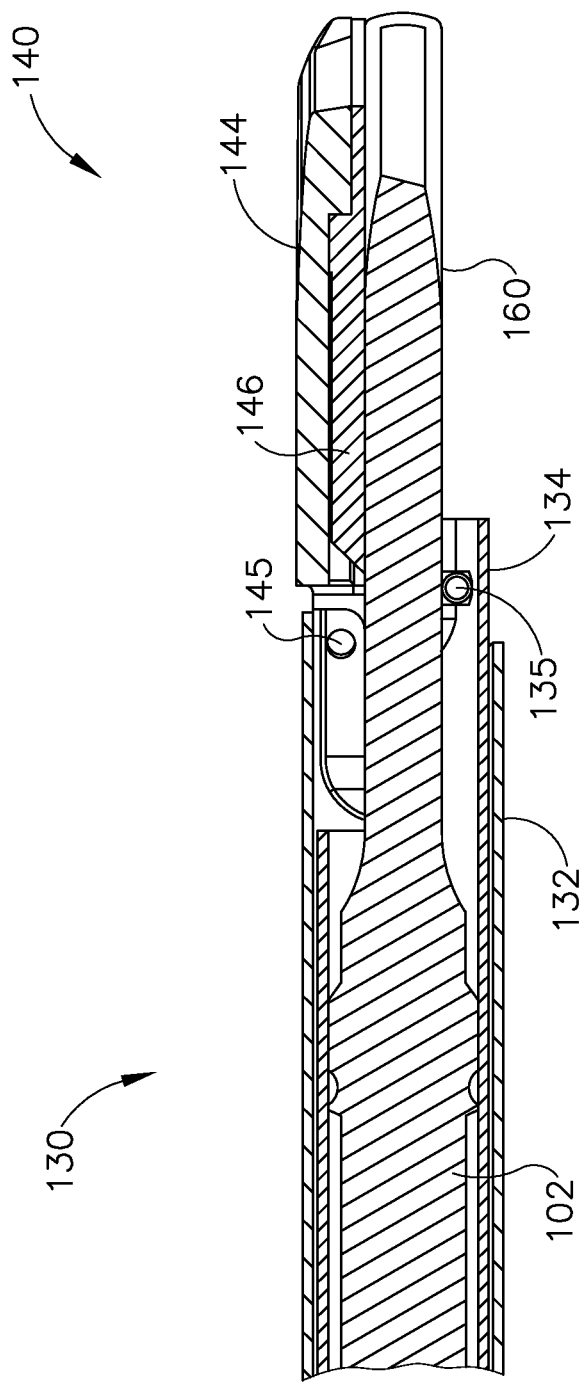
FIG. 3 depicts a cross-sectional side view of an end effector of the instrument of FIG. 2 in a closed position.
Figure 4:
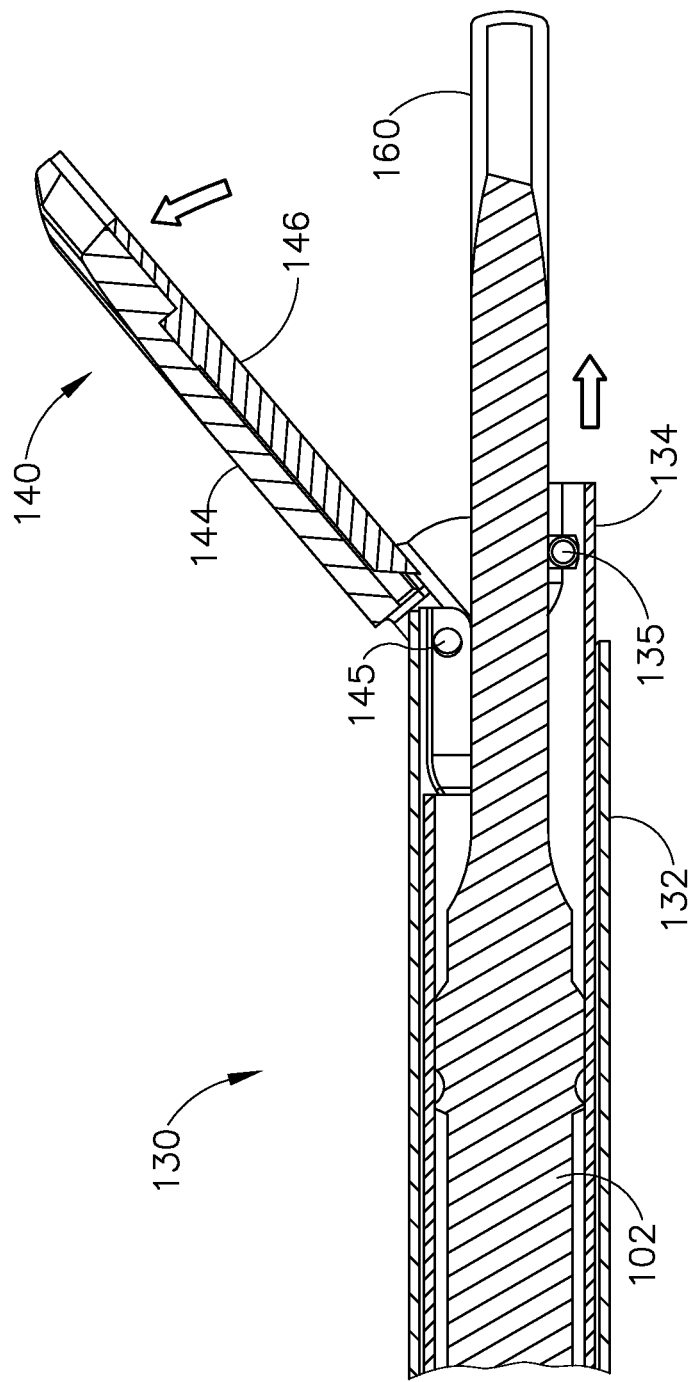
FIG. 4 depicts a cross-sectional side view of the end effector of FIG. 3 in an open position.

As shown in FIGS. 3 and 4, end effector (140) includes ultrasonic blade (160) and clamp arm (144). Clamp arm (144) includes a clamp pad (146) secured to an underside of clamp arm (144), facing blade (160). Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

Figure 5:
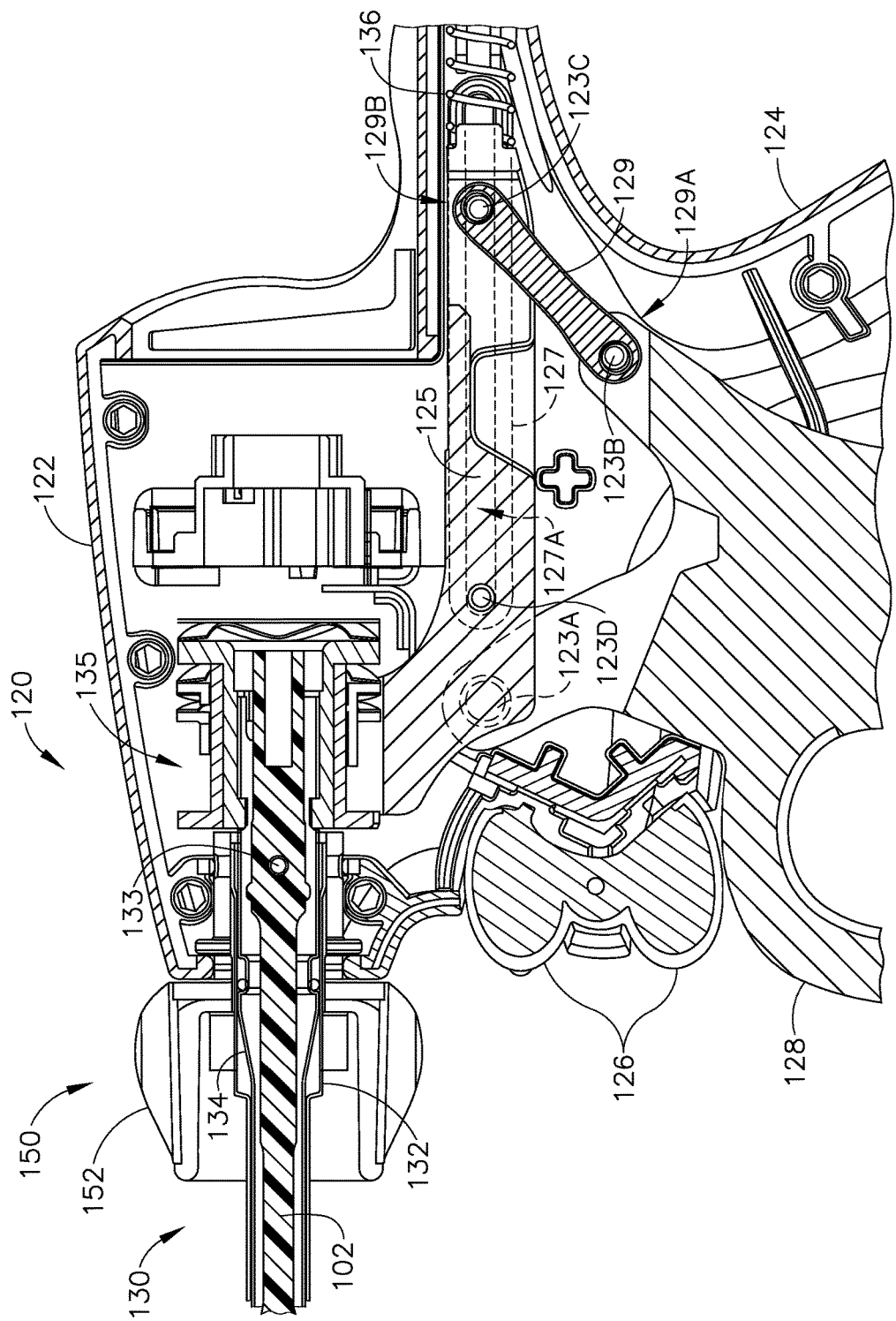
FIG. 5 depicts a cross-sectional side view of a handle assembly of the instrument of FIG. 2.
Figure 6:
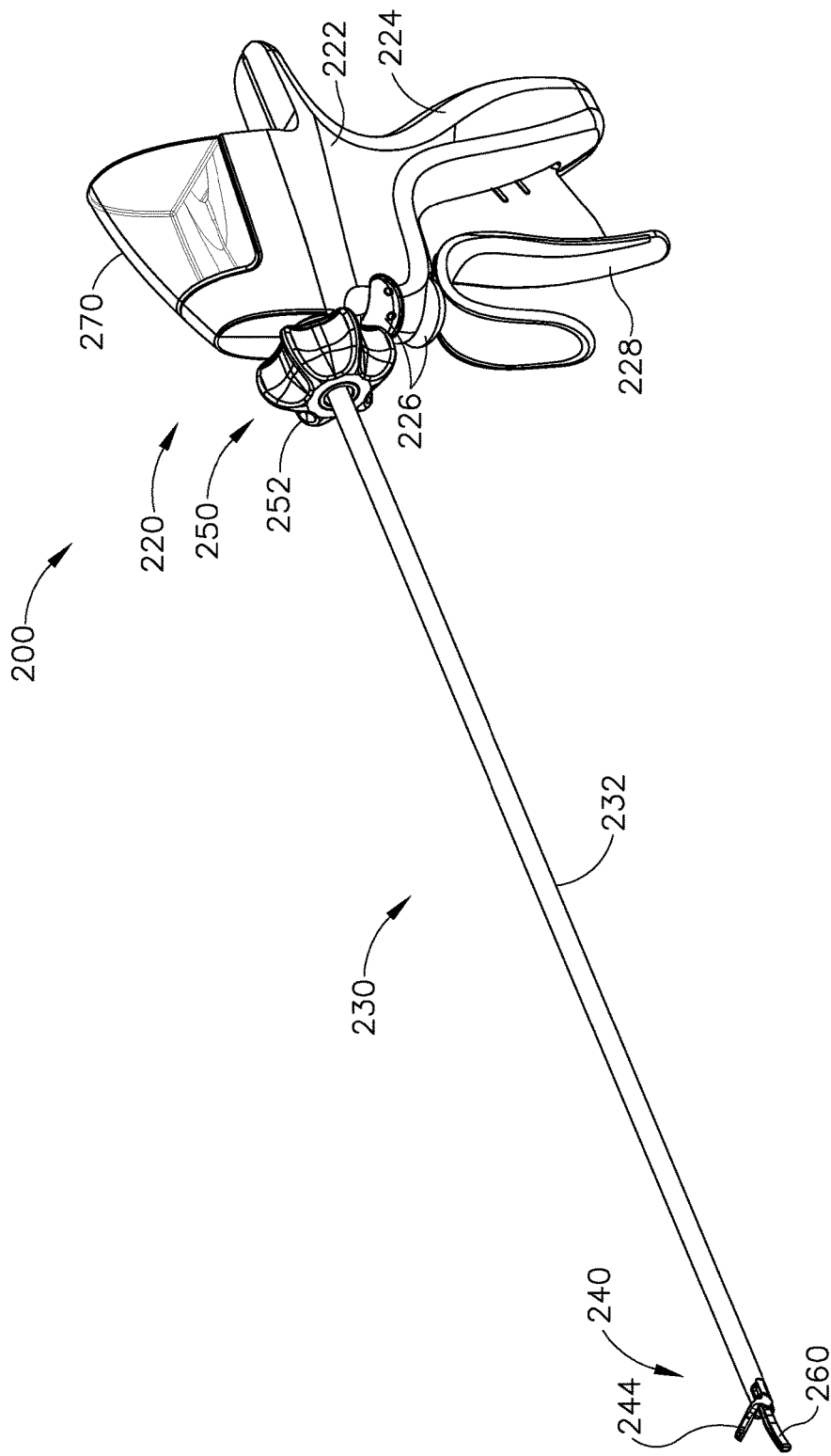
FIG. 6 depicts a perspective view of an exemplary alternative ultrasonic surgical instrument operable for use with the system of FIG. 1.
Figure 7:
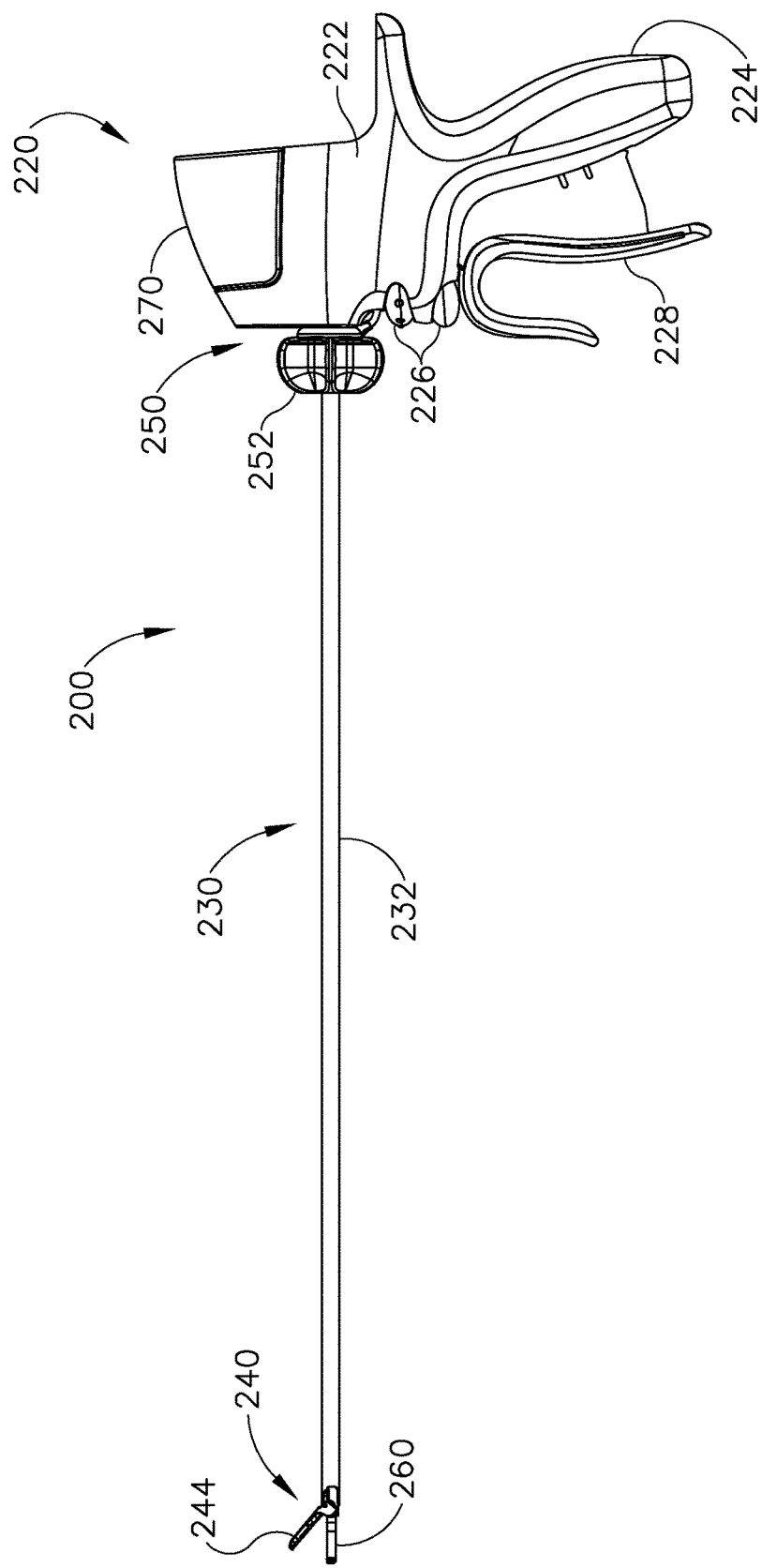
FIG. 7 depicts a side elevational view of the instrument of FIG. 6.
Figure 8:
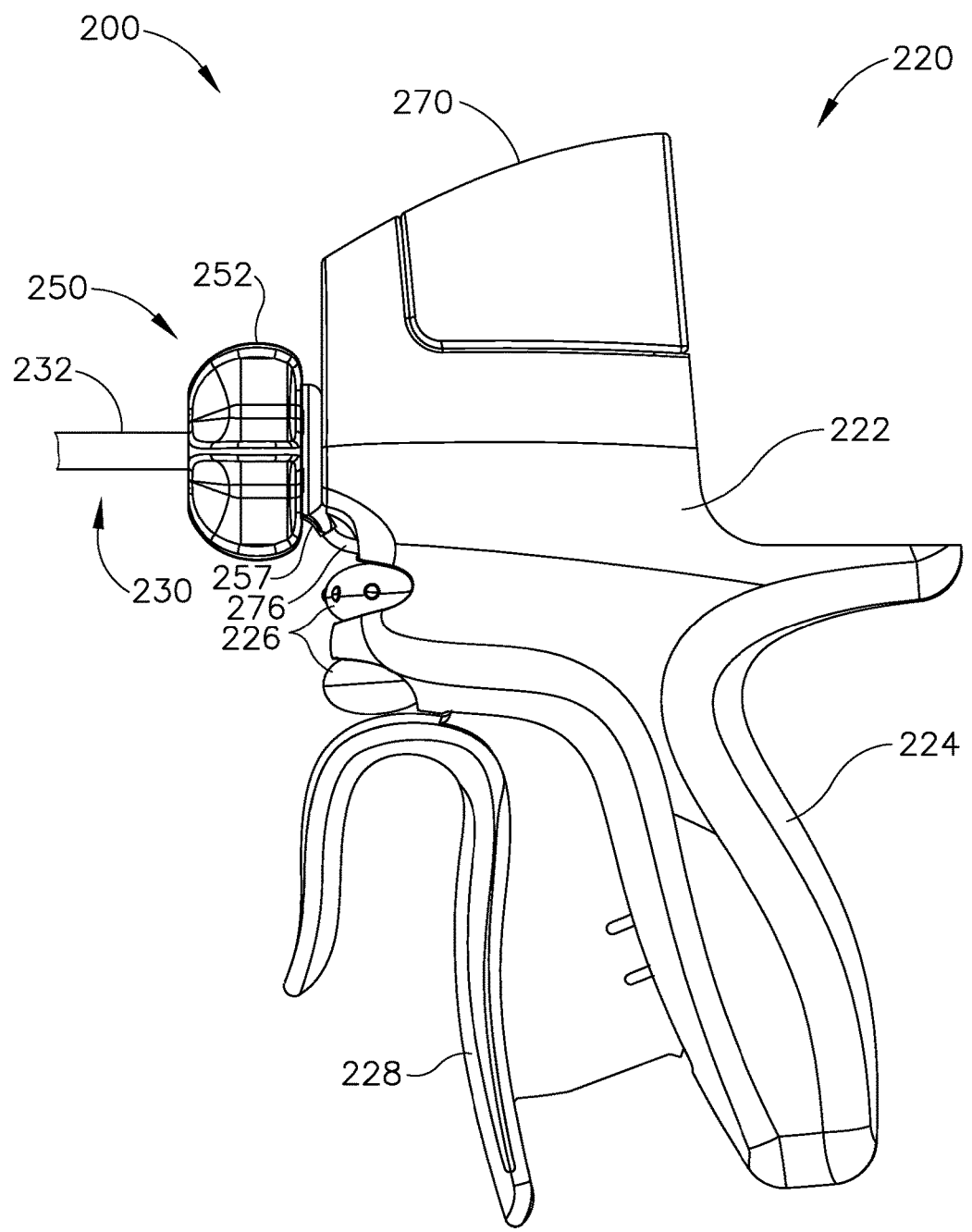
FIG. 8 depicts a side elevational view of a handle assembly of the instrument of FIG. 6.

As shown in FIG. 5, and as discussed above, handle (128) is pivotably coupled to handle assembly (120) via a pin (123A) such that handle (128) is operable to rotate about pin (123A). As will be described in more detail below, handle (128) is coupled with a yoke (125) via a linkage (129) such that rotation of handle (128) about pin (123A) causes longitudinal translation of yoke (125). A first end (129A) of linkage (129) is rotatably coupled with a proximal portion of handle (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of handle (128) is coupled with yoke (125) via linkage (129), pivoting of handle (128) toward and away from pistol grip (124) will cause longitudinal translation of yoke (125) within oval-shaped slots (127A). In particular, pivoting of handle (128) toward pistol grip (124) will cause proximal longitudinal translation of yoke (125) within oval-shaped slots (127A); and that pivoting of handle (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of handle (128) toward pistol grip (124) causes proximal longitudinal translation of yoke (125), it should be understood that pivoting of handle (128) toward pistol grip (124) will cause proximal longitudinal translation of inner tube (134) relative to outer sheath (132) and handle assembly (120); and because pivoting of handle (128) away from pistol grip (124) causes distal longitudinal translation of yoke (125), it should be understood that and that pivoting of handle (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of handle (128) toward pistol grip (124) will cause clamp arm (144) to move toward ultrasonic blade (160); and that pivoting of handle (128) away from pistol grip (124) will cause clamp arm (144) to move away from ultrasonic blade (160).

In some versions, one or more resilient members are used to bias clamp arm (144) and/or handle (128) to the open position shown in FIG. 4. For instance, as shown in FIG. 5, a spring (136) is positioned within a proximal end of body (122) of handle assembly (120). Spring (136) bears against body (122) and a proximal end of yoke (125) to thereby bias yoke (125) toward the distal position. Biasing of yoke (125) toward the distal position causes inner tube (134) to be biased distally and further causes handle (128) to be biased away from pistol grip (124).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940 now abandoned; U.S. Pub. No. 2010/0069940, issued as U.S. Pat. No. 9,023,071 May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. Exemplary Ultrasonic Surgical Instrument with Blade Cooling System

In some instances, one or more regions of instrument (20, 100) may heat up during extended operation of instrument (20, 100) in a surgical procedure. By way of example only, blade (24, 160), clamp arm (144), and/or other portions of instrument (20, 100) may eventually heat up over time. Such heating may be caused by friction and/or other factors. To the extent that the heat is initially generated in one particular component of instrument (20, 100) (e.g., blade (24, 160) or clamp arm (144), etc.), such heat may be gradually transmitted to other portions of instrument (20, 100). It may be desirable to minimize such heating and/or otherwise manage such heating in order to avoid having heated portions of instrument (20, 100) contact tissue that should not be heated. For instance, the operator may wish for end effector (140) to be relatively cool when the operator wishes to use end effector (140) to perform blunt dissections and/or simple tissue grasping, etc. It may also be desirable to minimize heat and/or otherwise manage heat in a way that does not significantly increase the size or adversely affect the operability of instrument (20, 100).

One merely exemplary way in which heat may be managed in instrument (20, 100) is to use a fluid to cool blade (24, 160). For instance, a cooling liquid (e.g., saline, etc.) may be applied to blade (24, 160) to thereby cool blade (24, 160). Various ways in which vapor and/or cooling fluid may be used to cool an ultrasonic blade are disclosed in U.S. patent application Ser. No. 14/552,530, entitled "Features to Apply Fluid to an Ultrasonic Blade of a Surgical Instrument," filed on even date herewith, the disclosure of which is incorporated by reference herein, issued as U.S. Pat. No. 10,034,685 on Jul. 31, 2018; U.S. patent application Ser. No. 14/553,329, entitled "Features to Drive Fluid toward an Ultrasonic Blade of a Surgical Instrument," filed on even date herewith, the disclosure of which is incorporated by reference herein, issued as U.S. Pat. No. 10,004,529 on Jun. 26, 2018; U.S. patent application Ser. No. 14/552,552, entitled "Shielding Features for Ultrasonic Blade of a Surgical Instrument," filed on even date herewith, the disclosure of which is incorporated by reference herein, issued as U.S. Pat. No. 9,993,260 on Jun. 12, 2018; and U.S. patent application Ser. No. 14/553,142, entitled "Features for Communication of Fluid through Shaft Assembly of Ultrasonic Surgical Instrument," filed on even date herewith, the disclosure of which is incorporated by reference herein, issued as U.S. Pat. No. 10,206,705 on Feb. 19, 2019. The examples described below provide various other structures and techniques through which a cooling fluid may be communicated to an ultrasonic blade such as blade (24, 160). While various examples of features configured to cool blade (24, 160) will be described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

FIGS. 6-22B illustrate an exemplary ultrasonic surgical instrument (200) that is configured to operate substantially similar to instrument (100) discussed above except for the differences discussed below. Instrument (200) of the present example comprises a handle assembly (220), a shaft assembly (230), and an end effector (240). Handle assembly (220) comprises a body (222) including a pistol grip (224) and a pair of buttons (226). Body (222) of handle assembly (220) is configured to receive an ultrasonic transducer assembly (212). Handle assembly (220) also includes a trigger (228) that is pivotable toward and away from pistol grip (224). End effector (240) includes an ultrasonic blade (260) and a pivoting clamp arm (244). Blade (260) is positioned at the distal end of an acoustic drivetrain. This acoustic drivetrain includes transducer assembly (212) and an acoustic waveguide (202), which mechanically and acoustically couples ultrasonic transducer (212) with blade (260). Clamp arm (244) is coupled with trigger (228) such that clamp arm (244) is pivotable toward ultrasonic blade (260) in response to pivoting of trigger (228) toward pistol grip (224); and such that clamp arm (244) is pivotable away from ultrasonic blade (260) in response to pivoting of trigger (228) away from pistol grip (224). In some versions, one or more resilient members are used to bias clamp arm (244) and/or trigger (228) to an open position.

Figure 9:
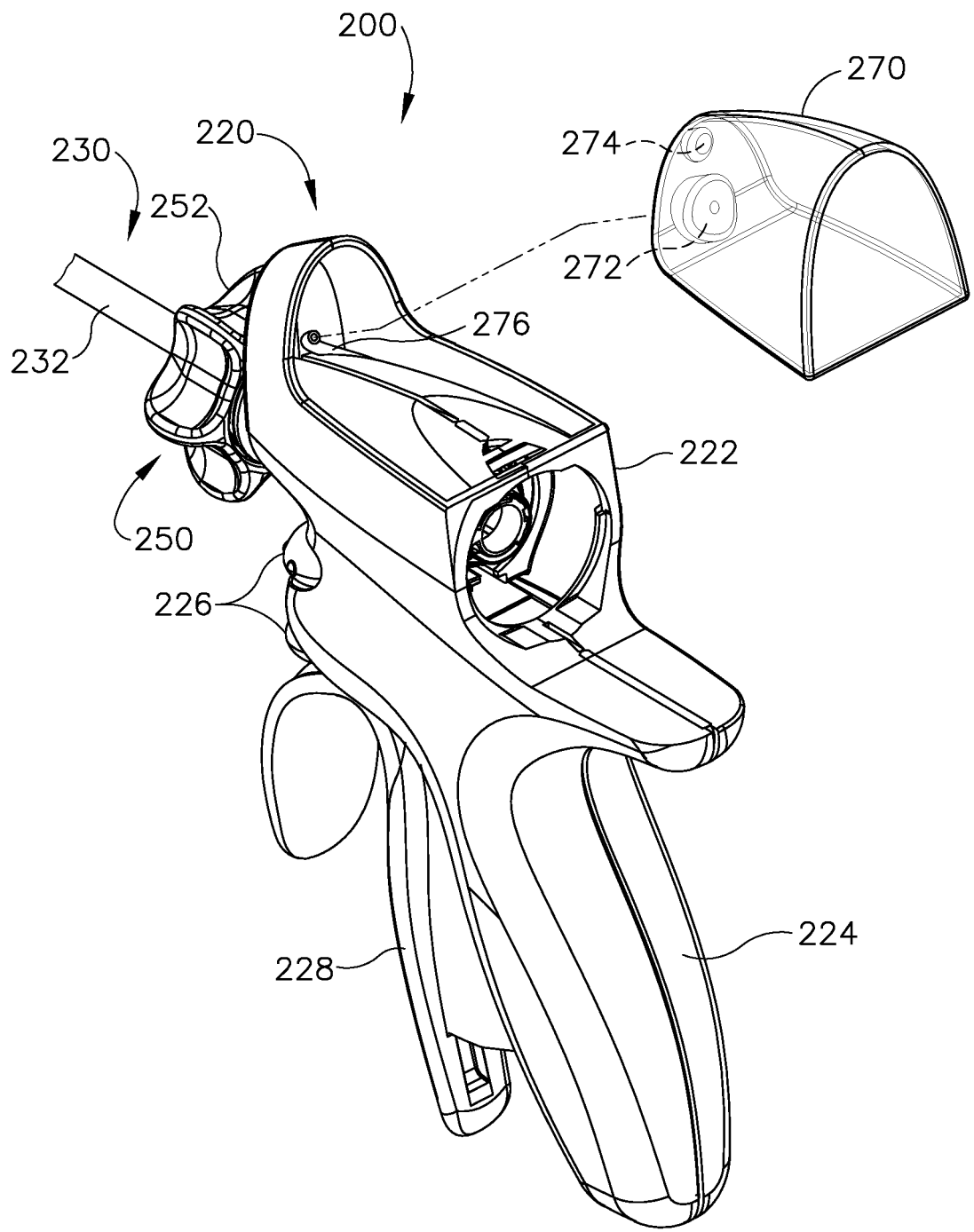
FIG. 9 depicts a perspective view of the handle assembly of FIG. 8 with a fluid reservoir of the handle assembly detached from the handle assembly.
Figure 10:
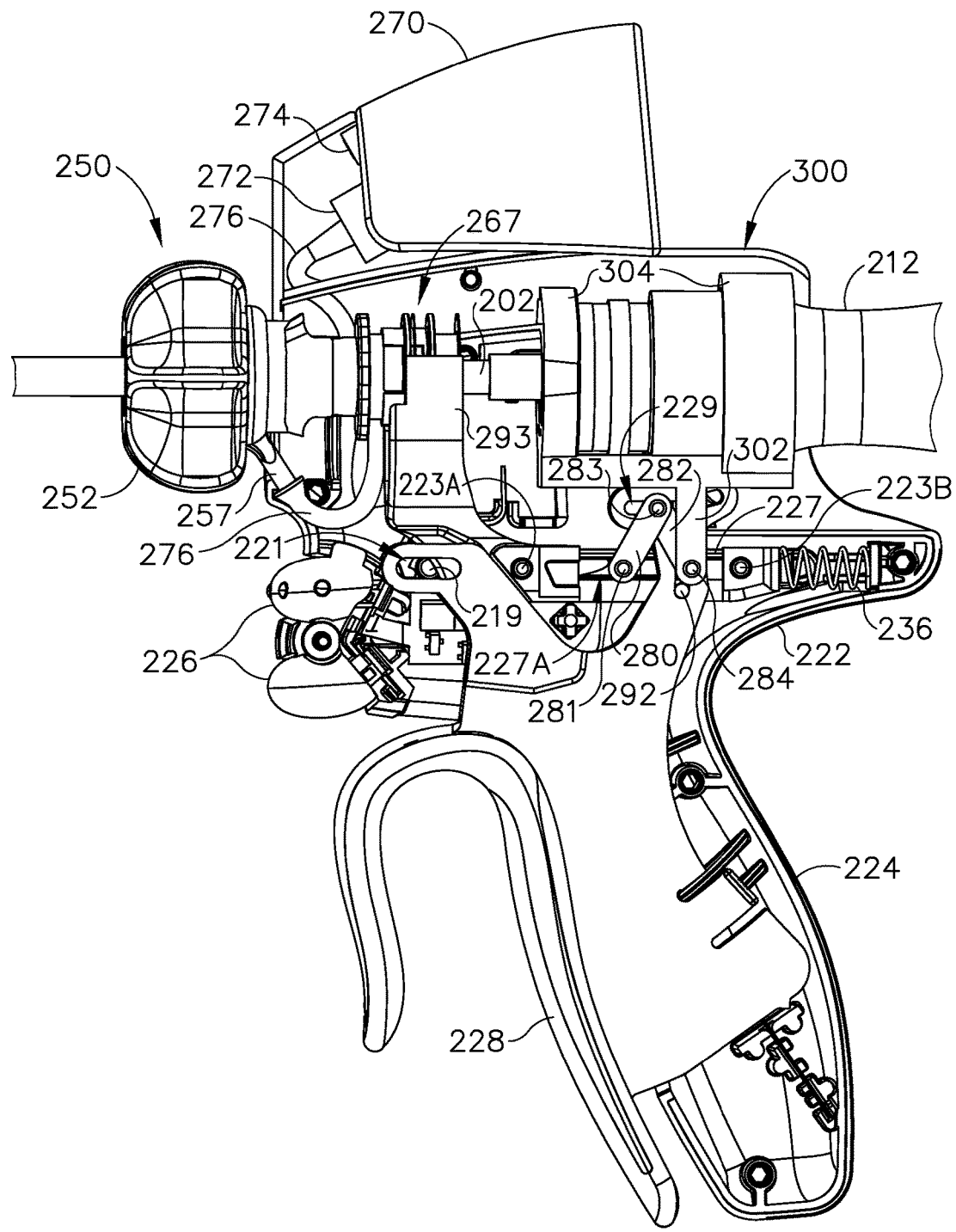
FIG. 10 depicts a side elevational view of the handle assembly of FIG. 6 with a housing shroud removed.

Handle assembly (220) of the present example further comprises a fluid reservoir (270). Fluid reservoir (270) is configured to be filled with liquid coolant (e.g., saline) and to selectively retain the liquid coolant therein. By way of example only, fluid reservoir (270) may be configured to hold approximately 26 cubic centimeters of fluid. Alternatively, fluid reservoir (270) may have any other suitable capacity. Fluid reservoir (270) is configured to selectively couple with a top portion of body (222) of handle assembly (220). In some instances, fluid reservoir (270) may couple with body (222) in a snap-fit manner. Alternatively, fluid reservoir (270) may be coupled with body (222) in any other suitable manner as would be apparent to one of ordinary skill in the art in view of the teachings herein. As best seen in FIGS. 9-10, fluid reservoir (270) comprises a valve (272) and a vent (274) formed in a distal portion of fluid reservoir (270).

With fluid reservoir (270) coupled to body (222), valve (272) is configured to couple with a tube (276), as best seen in FIG. 10. As will be discussed in more detail below, fluid reservoir (270) is configured to provide liquid coolant to a distal portion of shaft assembly (230) via tube (276) to thereby cool blade (260). Liquid coolant from fluid reservoir (270) may be provided to the distal portion of shaft assembly (230) by any suitable means. For instance, liquid coolant may be gravity-fed from fluid reservoir (270) to the distal portion of shaft assembly (230). Additionally or alternatively, liquid coolant may be drawn/driven from fluid reservoir (270) and passed to the distal portion of shaft assembly (230) by way of a pump (e.g., a piston pump, a peristaltic pump, etc.). By way of example only, instrument (200) may be constructed and operable to drive liquid coolant in accordance with at least some of the teachings of U.S. patent application Ser. No. 14/553,329, entitled "Features to Drive Fluid Toward an Ultrasonic Blade of a Surgical Instrument," filed on even date herewith, the disclosure of which is incorporated by reference herein, issued as U.S. Pat. No. 10,004,529 on Jun. 26, 2018. As liquid coolant is communicated from fluid reservoir (270), vent (274) permits atmospheric air to flow into fluid reservoir (270) to thereby prevent formation of a vacuum within fluid reservoir (270).

Figure 12:
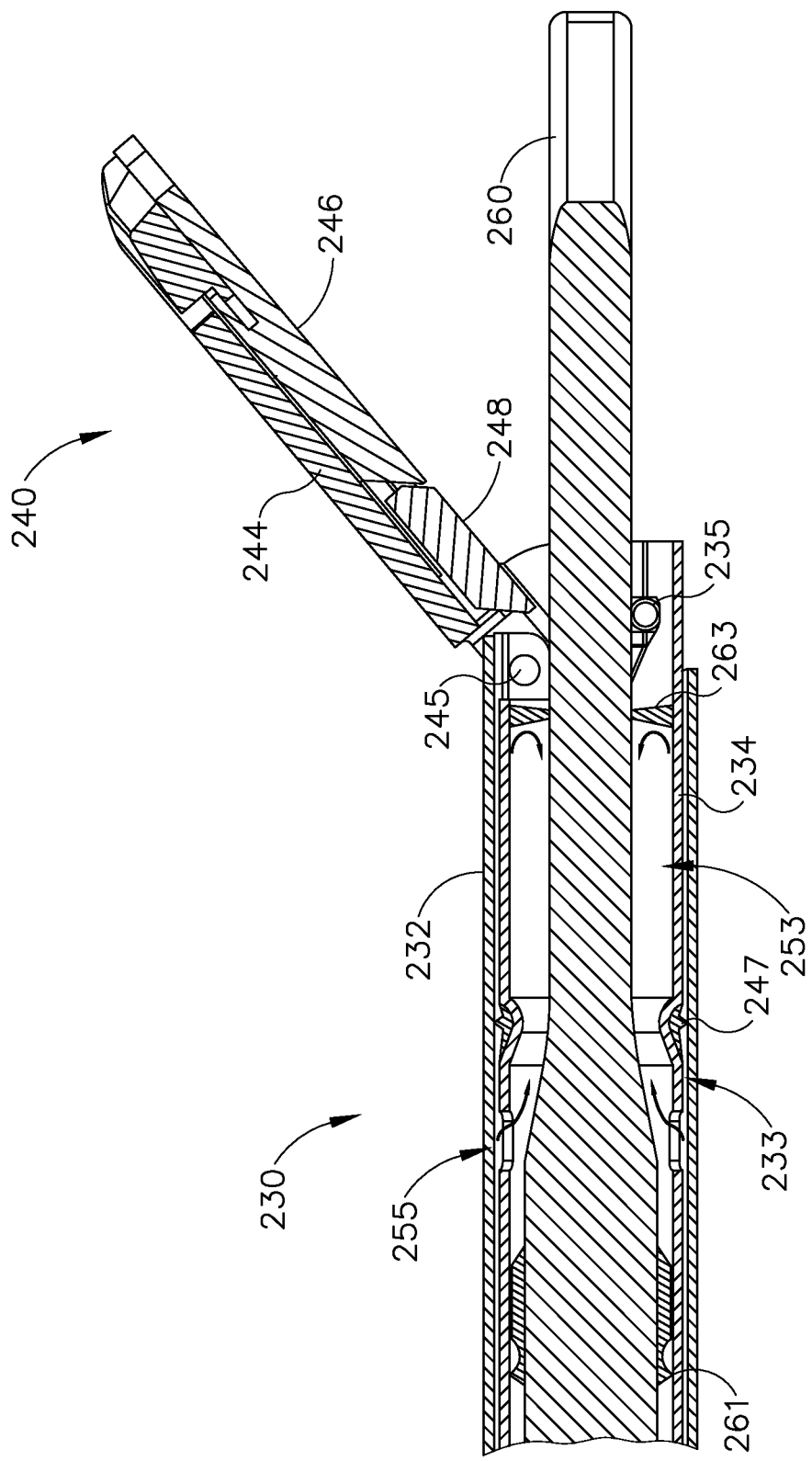
FIG. 12 depicts a cross-sectional side view of an end effector of the instrument of FIG. 6.

Shaft assembly (230) of the present example comprises an outer sheath (232) and an inner tube (234). Inner tube (234) is slidably disposed within outer sheath (232). As with shaft assembly (130) discussed above, inner tube (234) is operable to translate longitudinally within outer sheath (232) relative to outer sheath (232) to selectively pivot clamp arm (244) toward and away from blade (260). As best seen in FIG. 12, end effector (240) of the present example comprises clamp arm (244) and ultrasonic blade (260). Clamp arm (244) includes a primary clamp pad (246) and a secondary clamp pad (248) that are secured to an underside of clamp arm (244), facing blade (260). Clamp arm (244) is operable to selectively pivot toward and away from blade (260) to selectively clamp tissue between clamp pads (246, 248) and blade (260). Clamp arm (244) is pivotably coupled with a distal end of outer sheath (232) of shaft assembly (230), above ultrasonic blade (160), via a pin (245). A distal end of inner tube (234) is rotatably coupled with a proximal end of clamp arm (244), below ultrasonic blade (260), via a pin (235) such that longitudinal translation of inner tube (234) causes rotation of clamp arm (244) about pin (245) toward and away from ultrasonic blade (260) to thereby clamp tissue between clamp pads (246, 248) and ultrasonic blade (260) to cut and/or seal the tissue. In particular, proximal longitudinal translation of inner tube (234) relative to outer sheath (232) and handle assembly (220) causes clamp arm (244) to move toward ultrasonic blade (260); and distal longitudinal translation of inner tube (234) relative to outer sheath (232) and handle assembly (220) causes clamp arm (244) to move away from ultrasonic blade (260).

Figure 11:
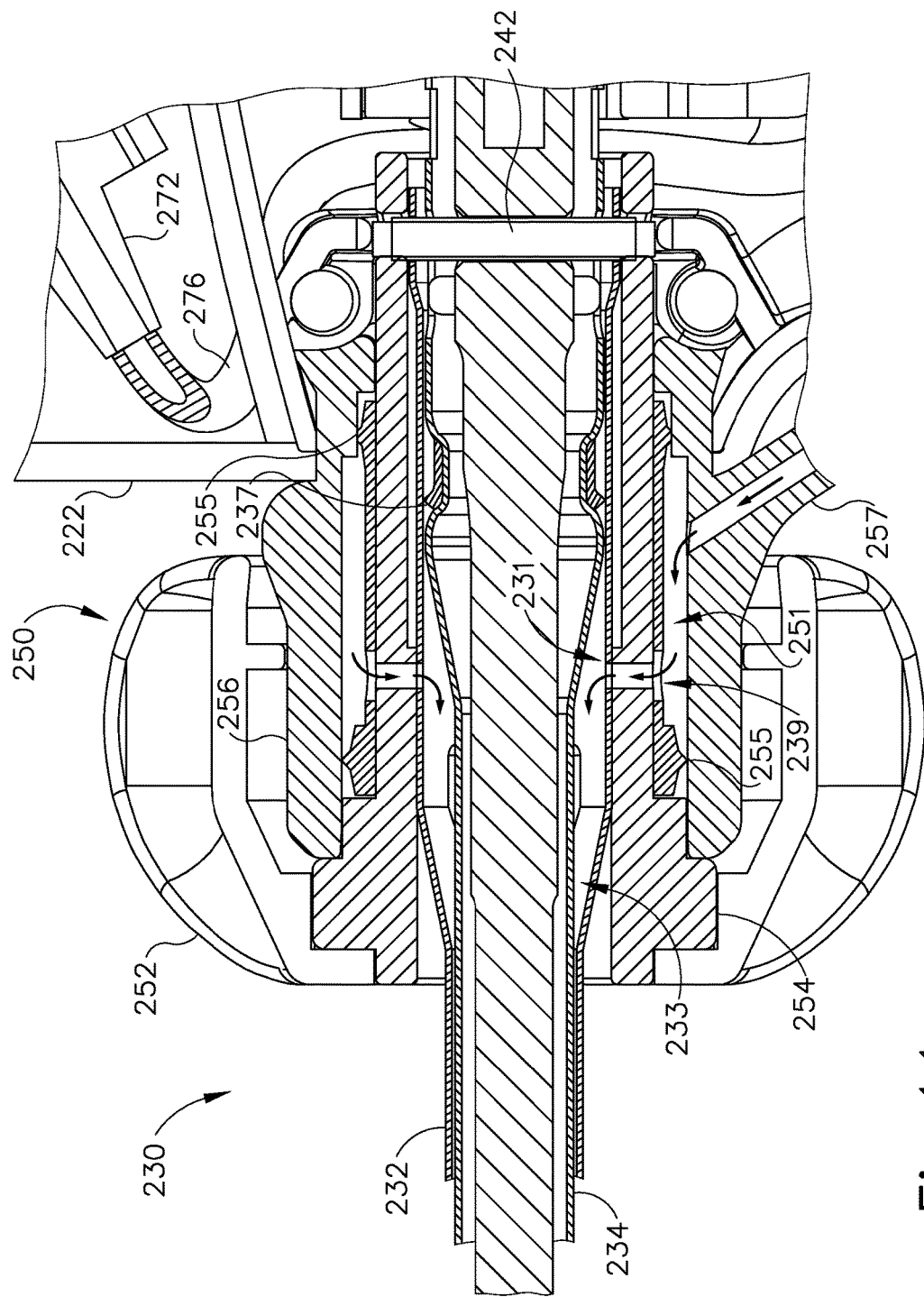
FIG. 11 depicts a detailed cross-sectional side view of a rotation assembly of the instrument of FIG. 6.

Shaft assembly (230) of the present example further includes a rotation assembly (250). Rotation assembly (250) is operable to rotate the entire shaft assembly (230) and end effector (240) relative to handle assembly (220) about a longitudinal axis of shaft assembly (230). Rotation assembly (250) comprises a rotation knob (252) and a rotation housing (254). Rotation knob (252) is coupled with rotation housing (254) such that rotation of rotation knob (252) causes concurrent rotation of rotation housing (254). Rotation housing (254) is coaxially disposed about shaft assembly (230) and is coupled thereto via a pin (242). As best seen in FIG. 11, pin (242) passes through rotation housing (254), shaft assembly (230), and waveguide (202) such that rotation of rotation housing (254) causes concurrent rotation of shaft assembly (230), waveguide (202), and end effector (240). Thus, it should be understood that rotation of rotation knob (252) is operable to cause concurrent rotation of shaft assembly (230), waveguide (202), and end effector (240). Pin (242) is located at a position along the length of waveguide (202) corresponding to a node associated with resonant ultrasonic vibrations communicated through waveguide (202).

Rotation assembly (250) further comprises a stationary housing (256). Stationary housing (256) is secured to distal end of body (222) of handle assembly (220). Rotation knob (252) and rotation housing (254) are rotatably coupled to stationary housing (256) such that rotation knob (252) and rotation housing (254) are operable to rotate relative to stationary housing (256). An interior space (251) is defined between an interior surface of stationary housing (256) and an exterior surface of rotatable housing (254). As best seen in FIG. 10, stationary housing (256) comprises a tubular inlet (257) extending from an exterior surface of stationary housing (256). Tubular inlet (257) provides fluid access to interior space (251) such that fluid may pass through tubular inlet (257) into interior space (251). Tube (276) is in fluid communication with tubular inlet (257) such that liquid coolant from fluid reservoir (270) may pass through tube (276) into interior space (251) via tubular inlet (257). By way of example only, a fluid pump, one or more valves, and/or various other components (e.g., as described in one or more references cited herein, etc.) may be used to provide and/or regulate communication of liquid coolant from tube (276) to tubular inlet (257). A pair of annular seal rings (255) are disposed about an exterior surface of rotation housing (254) within interior space (251). Seal rings (255) are configured to engage an interior surface of stationary housing (256) to thereby provide a fluid seal between rotation housing (254) and stationary housing (256) so as to prevent fluid from inadvertently escaping interior space (251).

An interior space (233) is formed between outer sheath (232) and inner tube (234) and extends substantially the length of shaft assembly (230). As will be discussed in more detail below, liquid coolant is configured to pass within interior space (233) to a distal portion of shaft assembly (230) to thereby cool blade (260). As shown in FIG. 11, a pair of openings (239) are formed in rotation housing (254), and another pair of openings (231) are formed in a proximal portion of outer sheath (232). Openings (231, 239) are aligned so as to provide fluid communication between interior space (251) and interior space (233) such that the liquid coolant is able to pass through openings (231, 239) from interior space (251) into interior space (233). It should be understood that any other suitable number of openings (231, 239) may be provided. An annular seal ring (237) is disposed about an exterior surface of inner tube (234), within interior space (233), proximal openings (231, 239). Seal ring (237) is configured to engage an interior surface of outer sheath (232) to thereby provide a fluid seal between inner tube (234) and outer sheath (232) so as to prevent fluid from inadvertently escaping proximally from interior space (233).

As shown in FIG. 12, as liquid coolant is passed within interior space (233) of shaft assembly (230), the liquid coolant passes from interior space (233) into an interior space (253) of inner tube (234) via a pair of openings (255) that are formed in a distal portion of inner tube (234). Of course, any suitable number of openings (255) may be provided. An annular seal ring (247) is disposed about an exterior surface of inner tube (234), within interior space (233), distal to openings (255). Seal ring (247) is configured to engage an interior surface of outer sheath (232) to thereby provide a fluid seal between inner tube (234) and outer sheath (232) so as to prevent fluid from inadvertently escaping distally from interior space (233). An annular seal ring (261) is disposed about an exterior surface of waveguide (202) within interior space (253). Seal ring (261) is located proximal to openings (255). Circular seal ring (261) is configured to engage an interior surface of inner tube (234) to thereby provide a fluid seal between waveguide (202) and inner tube (234) so as to prevent fluid from inadvertently escaping proximally from interior space (253).

In the present example, another circular seal ring (263) is disposed about the interior surface of inner tube (234) within interior space (253). Circular seal ring (263) is located distal to openings (255). Circular seal ring (263) is configured to engage the exterior surface of waveguide (202) to thereby provide a fluid seal between waveguide (202) and inner tube (234) so as to prevent fluid from inadvertently escaping distally from interior space (253). Circular seal rings (261, 263) are located at positions along the length of waveguide (202) corresponding to a node associated with resonant ultrasonic vibrations communicated through waveguide (202). Circular seal ring (263) is merely optional, such that circular seal ring (263) may be omitted if desired. In versions where circular seal ring (263) is omitted, liquid coolant may ultimately reach the surgical site. However, this may not be a problem, particularly when the liquid coolant comprises a biologically benign solution (e.g., saline, etc.).

It should be understood from the discussion above that liquid coolant may be communicated from fluid reservoir (270), through tube (276) and shaft assembly (230), and into interior space (253) of inner tube (234). As will be discussed in more detail below, blade (260) is configured to be translated longitudinally proximally relative to shaft assembly (230) into interior space (253) of inner tube (234), such that the liquid coolant within interior space (253) contacts blade (260) to thereby cool blade (260).

Figure 13:
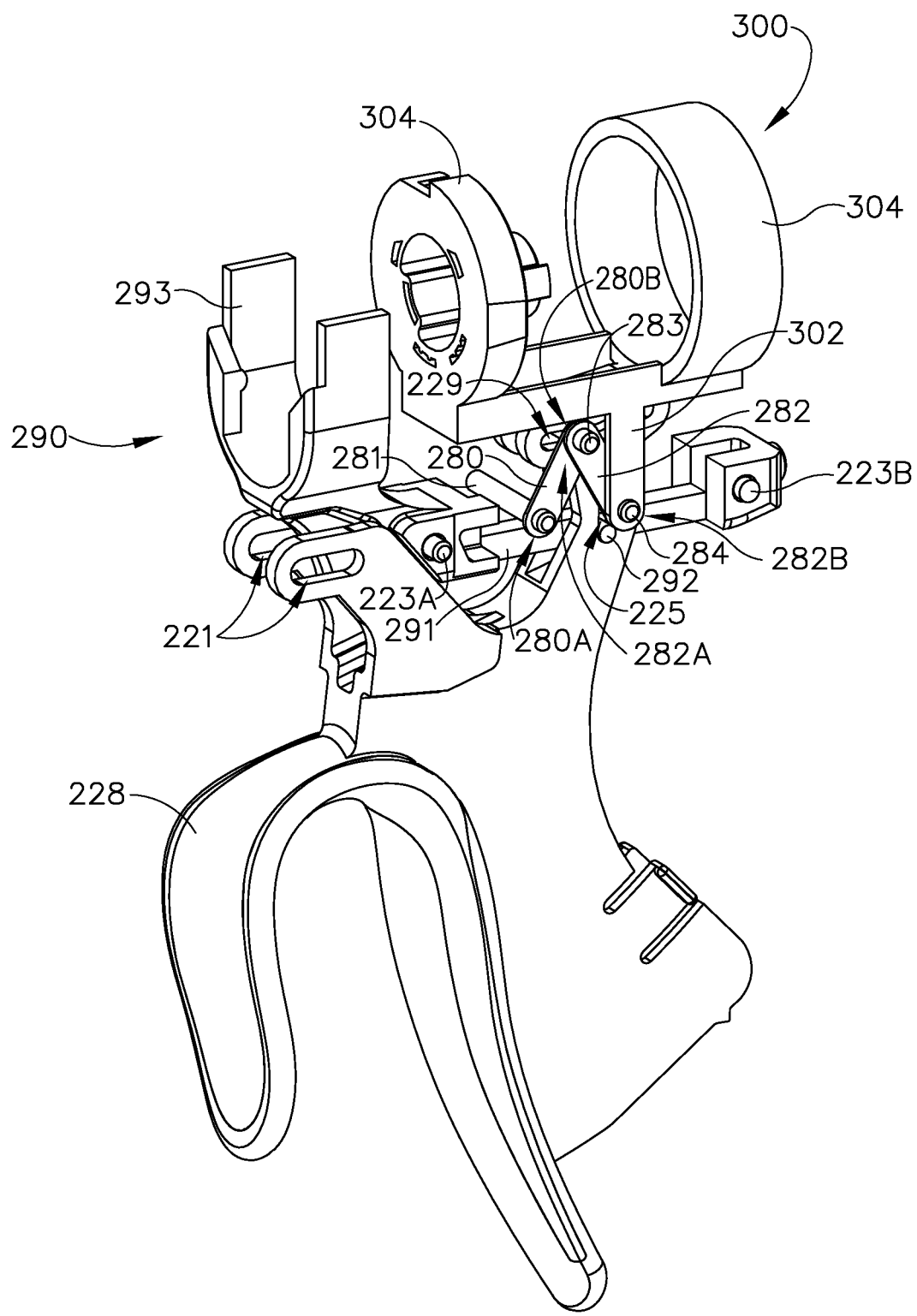
FIG. 13 depicts a perspective view of an actuation assembly of the instrument of FIG. 6.
Figure 14:
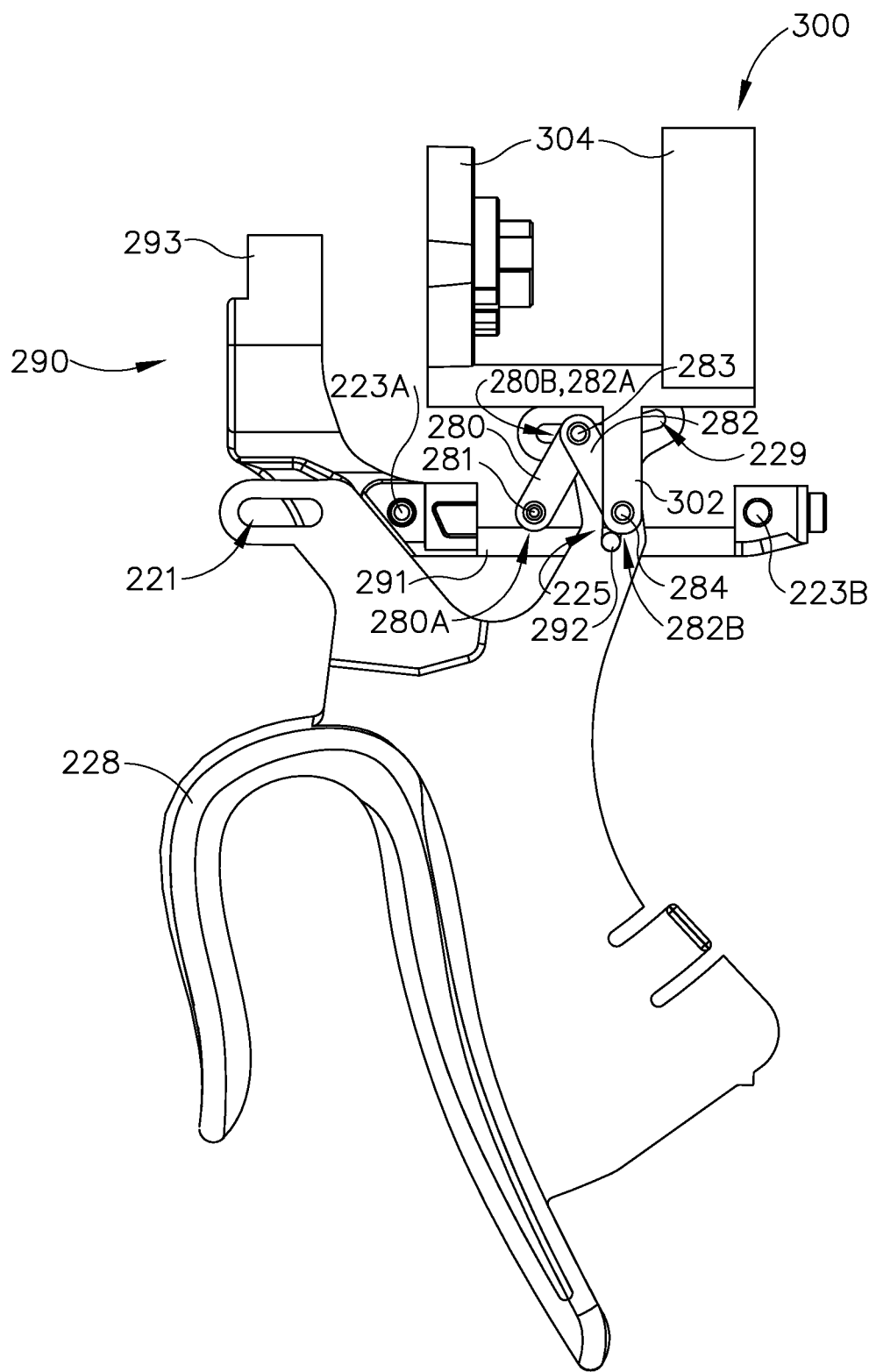
FIG. 14 depicts a side elevational view of the actuation assembly of FIG. 13.
Figure 15:
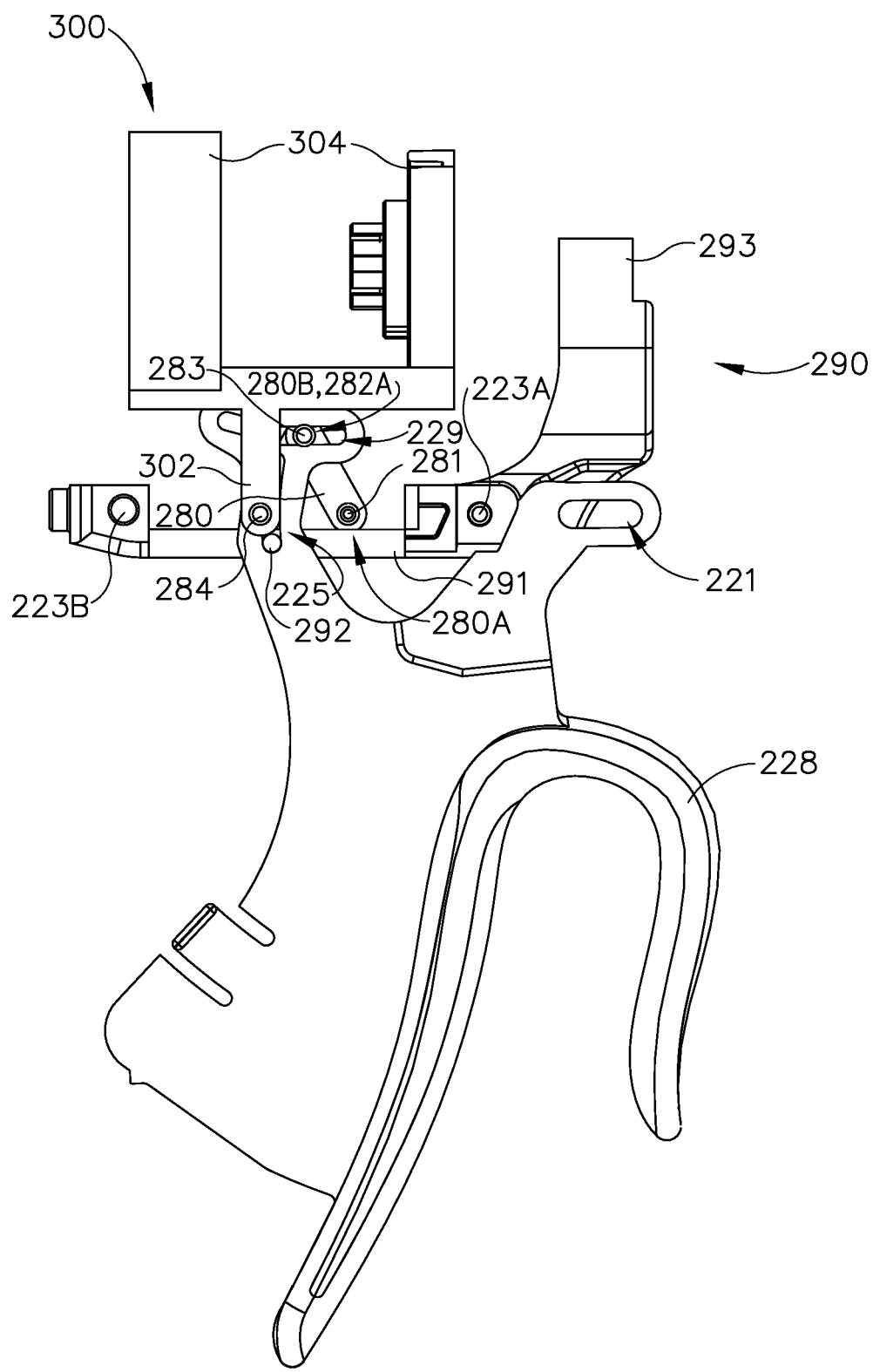
FIG. 15 depicts another side elevational view of the actuation assembly of FIG. 13.

FIGS. 10, 13-19B, 21A, and 21B show interior components of handle assembly (220) including an actuation assembly (295) shown in FIGS. 13-15. Trigger (228) of handle assembly (220) is pivotably and slidably coupled to body (222) of handle assembly (220). In particular, a pair of pins (219), which extend inwardly from opposing interior surfaces of body (222), are slidably and rotatably disposed within a pair of elongate slots (221) formed in a distal portion of trigger (228). Thus, trigger (228) is operable to translate toward and away from pistol grip (224) as pins (219) slide within slots (221); and trigger (228) is further operable to pivot toward and away from pistol grip (224) as pins (219) rotate within slots (221).

Figure 17:
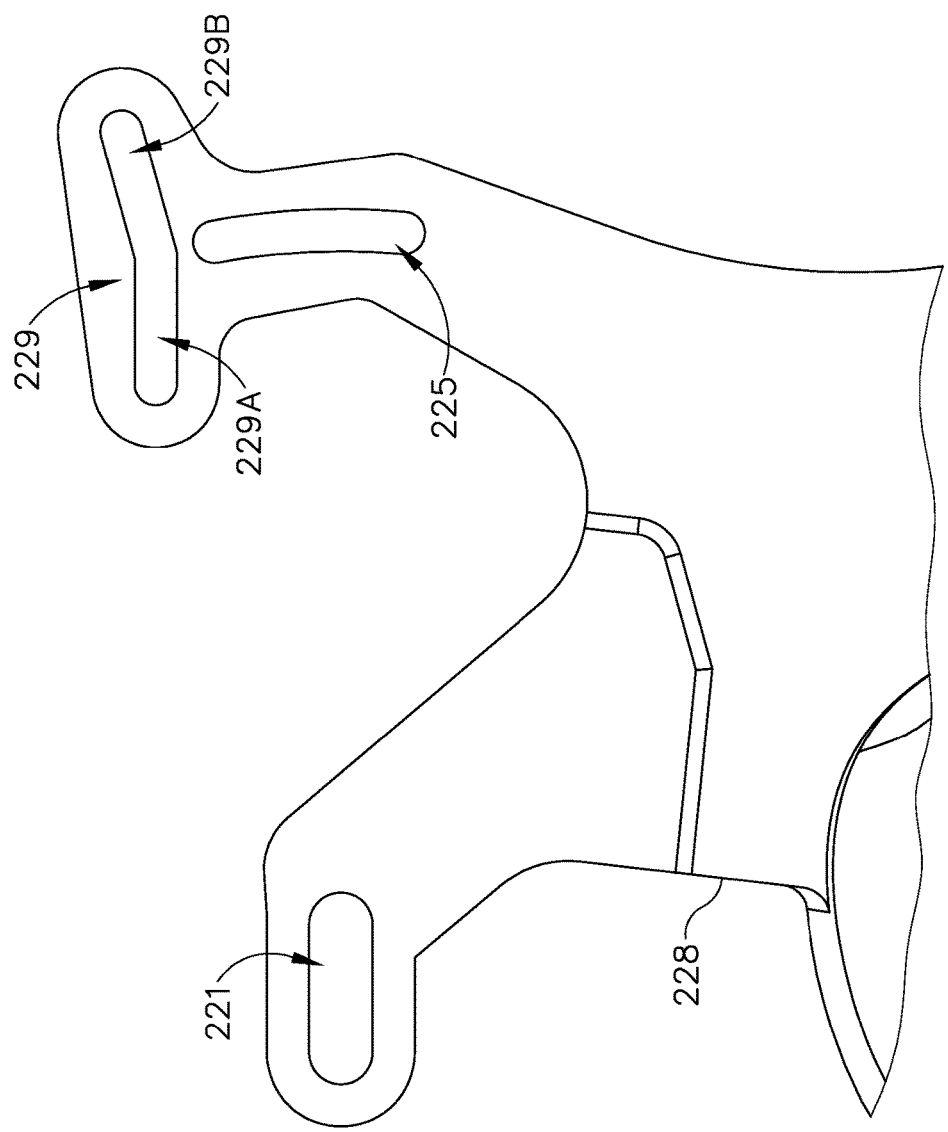
FIG. 17 depicts a detailed side elevational view of a trigger of the actuation assembly of FIG. 13.
Figure 18:
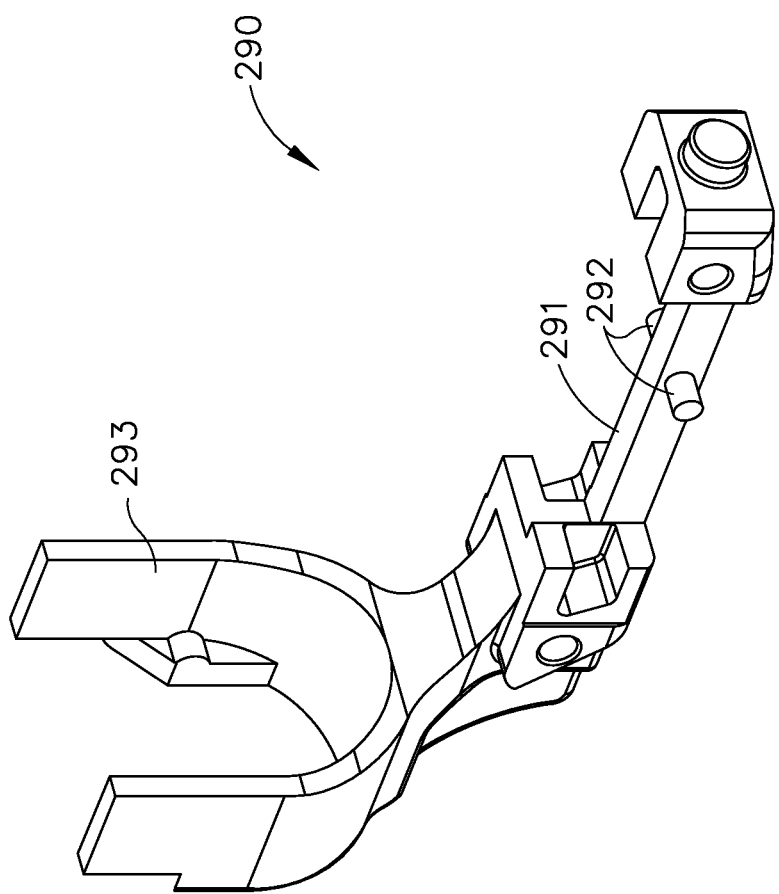
FIG. 18 depicts a perspective view of a yoke of the actuation assembly of FIG. 13.

As will be described in more detail below, trigger (228) is coupled with a yoke (290) such that translation of trigger (228) toward and away from pistol grip (224) causes translation of yoke (290) within body (222). As best seen in FIG. 18, yoke (290) comprises a pair of pins (292) extending outwardly from an intermediate portion (291) of yoke (290). A fork member (293) extends upwardly from intermediate portion (291). Pins (292) are slidably and rotatably disposed within a pair of slots (225) that are formed in a proximal portion of trigger (228). Slots (225) are oriented such that translation of trigger (228) is communicated to yoke (290) via engagement between pins (292) and slots (225) to thereby cause concurrent translation of yoke (290). In particular, proximal translation of trigger (228) is causes concurrent proximal translation of yoke (228), and distal translation of trigger (228) is causes concurrent distal translation of yoke (228). As best seen in FIG. 17, slots (225) are curved such that pins (292) slide within slots (225) as trigger (228) is rotated toward and away from pistol grip (224). Thus, rotation or pivotal movement of trigger (228) is not communicated to yoke (290). Only translation of trigger (228) is communicated to yoke (290).

A pair of elongate projections (227) extend inwardly from interior surfaces of body (222). An interior surface of each elongate projection (227) defines an elongate slot (227A). A pair of pins (223A, 223B) pass completely through a proximal portion of yoke (290) and a distal portion of yoke (290) such that ends of pins (223A, 223B) extend from opposite sides of yoke (290). These ends of pins (223A, 223B) are slidably and rotatably disposed within elongate slots (227A). It should therefore be understood that yoke (290) is longitudinally translatable along elongate slots (227A) via pins (223A, 223B), between a distal longitudinal position (FIG. 21A) and a proximal longitudinal position (FIG. 21B). Furthermore, because trigger (228) is coupled with yoke (290) via pins (292), it should be understood that proximal translation of trigger (228) toward pistol grip (224) will cause proximal longitudinal translation of yoke (290) along elongate slots (227A); and that distal translation of trigger (228) away from pistol grip (224) will cause distal longitudinal translation of yoke (225) along elongate slots (227A).

Fork member (293) of yoke (290) is coupled with a coupling feature (267) that is fixedly secured to the proximal end of inner tube (234) of shaft assembly (230). Inner tube (234) thus translates unitarily with yoke (290). As discussed above, inner tube (234) is longitudinally translatable within outer sheath (232), such that inner tube (234) is configured to longitudinally translate concurrently with yoke (290). Furthermore, because proximal translation of trigger (228) toward pistol grip (224) causes proximal longitudinal translation of yoke (290), it should be understood that proximal translation of trigger (228) toward pistol grip (224) will cause proximal longitudinal translation of inner tube (234) relative to outer sheath (232) and handle assembly (220).

Because distal translation of trigger (228) away from pistol grip (224) causes distal longitudinal translation of yoke (290), it should be understood that and that distal translation of trigger (228) away from pistol grip (224) will cause distal longitudinal translation of inner tube (234) relative to outer sheath (232) and handle assembly (220). Finally, because longitudinal translation of inner tube (234) causes rotation of clamp arm (244) toward and away from blade (260) as discussed above, it should be understood that proximal translation of trigger (228) toward pistol grip (224) will cause clamp arm (244) to move toward ultrasonic blade (260) (FIG. 22A); and that distal translation of trigger (228) away from pistol grip (224) will cause clamp arm (244) to move away from ultrasonic blade (260) (FIG. 22B).

Figure 21A:
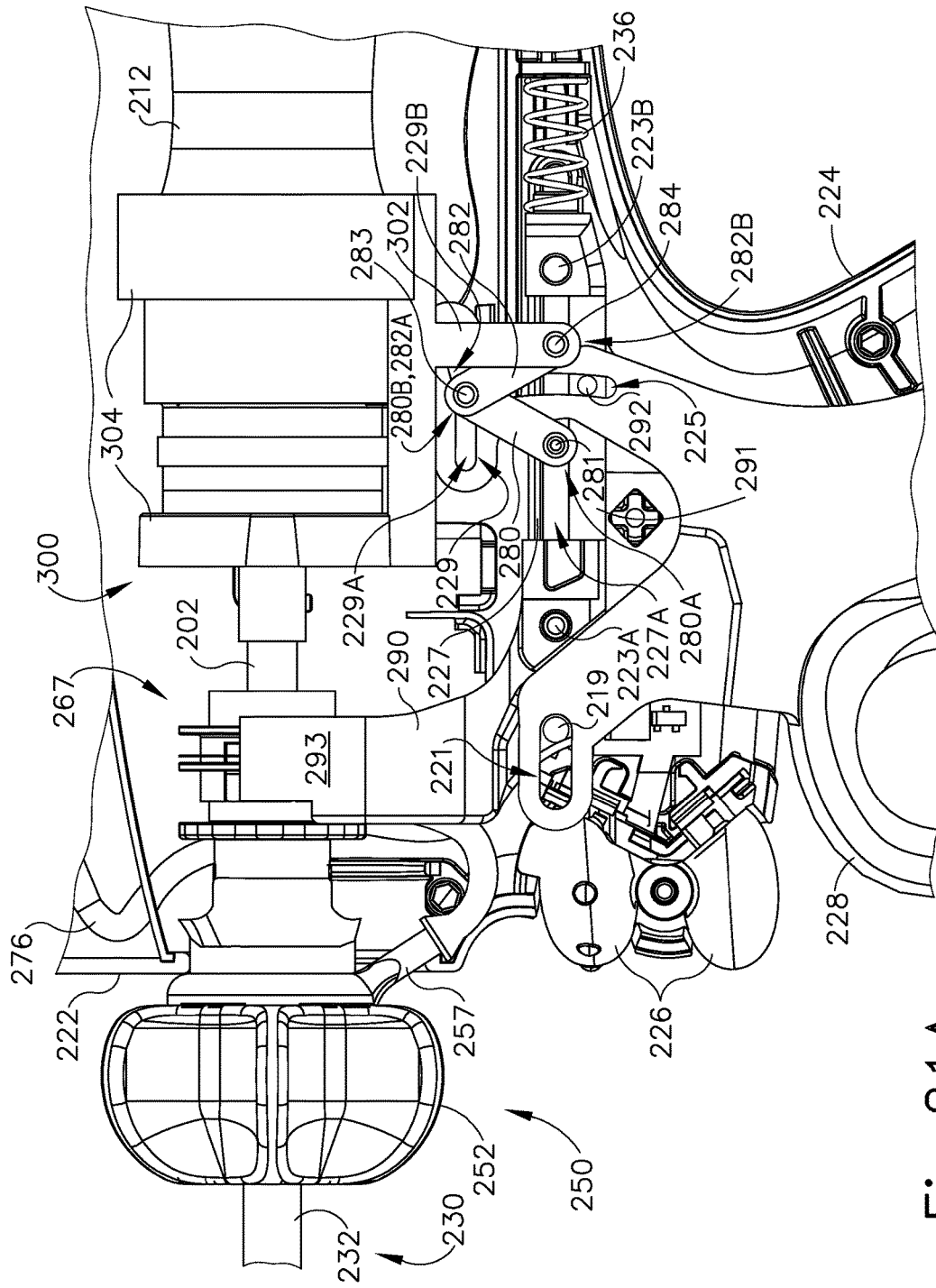
FIG. 21A depicts a side elevational view of the handle assembly of FIG. 8 with a housing shroud removed, with the trigger of FIG. 17 in the first position, and with the yoke of FIG. 18 and an inner tube of the instrument of FIG. 6 in a first position.
Figure 21B:
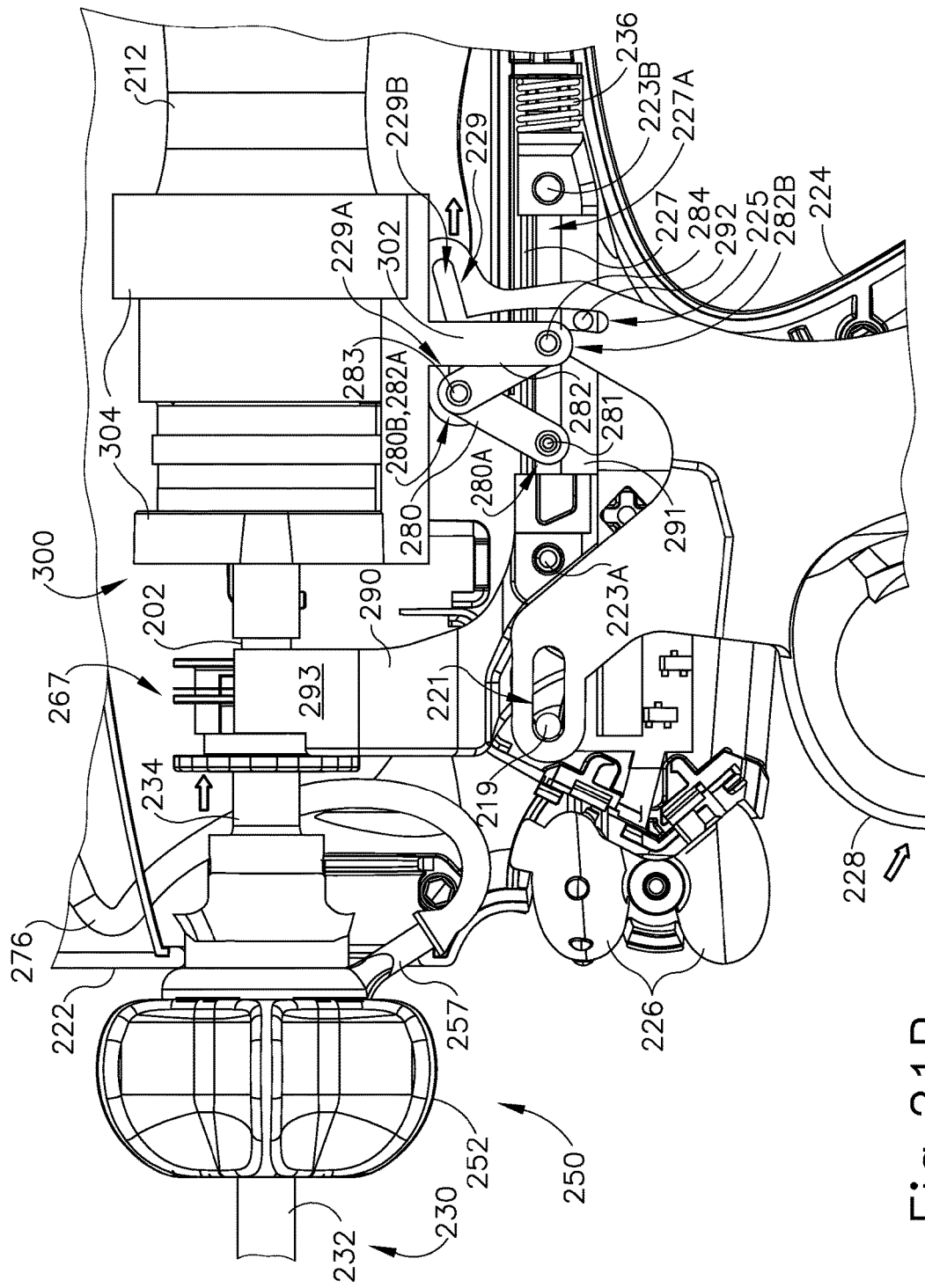
FIG. 21B depicts a side elevational view of the handle assembly of FIG. 8 with a housing shroud removed, with the yoke of FIG. 18 and the inner tube of FIG. 21A moved to a second position by translation of the trigger of FIG. 17 to a third position.
Figure 22A:
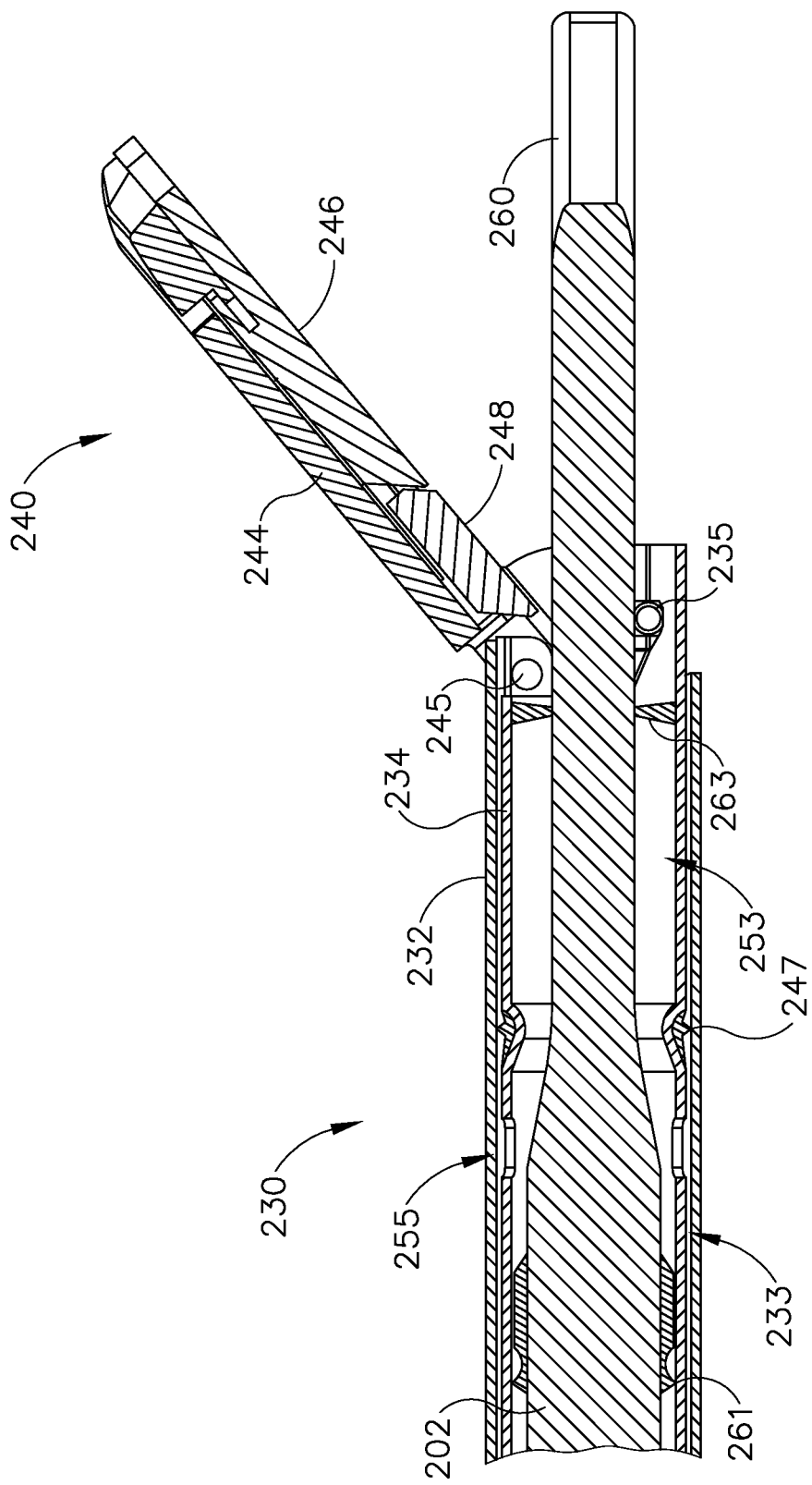
FIG. 22A depicts a cross-sectional side view of the end effector of FIG. 12 in the open position, with the inner tube of FIG. 21A in the first position.
Figure 22B:
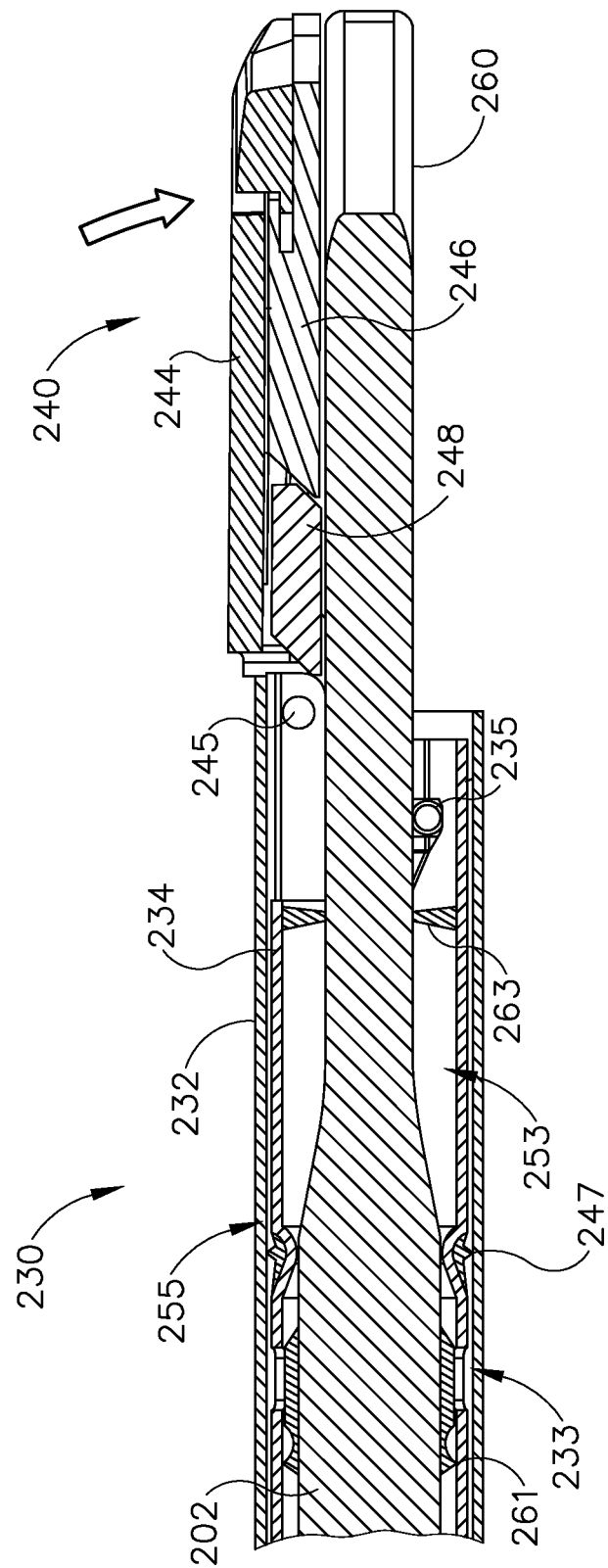
FIG. 22B depicts a cross-sectional side view of the end effector of FIG. 12 moved into the closed position by movement of the inner tube of FIG. 21A to the second position.

FIGS. 21A-22B show part of the operation of handle assembly (220). FIG. 21A shows trigger (228) in an initial position. In this position, yoke (290) is in a distal longitudinal position such that, as described above, clamp arm (244) is in an open position relative to blade (260) as shown in FIG. 22A. As trigger (228) is translated proximally toward pistol grip (224), engagement between pins (292) of yoke (290) and slots (225) of trigger (228) causes proximal longitudinal translation of yoke (290) as shown in FIG. 21B. Trigger (228) translates proximally along pins (219), such that pins (219) are positioned in the distal regions of slots (221) when trigger (228) reaches the proximally translated position. Proximal longitudinal translation of yoke (290) causes concurrent proximal longitudinal translation of inner tube (234) via the coupling between fork member (293) and coupling feature (267). Proximal longitudinal translation of inner tube (234) in turn causes clamp arm (244) to pivot toward blade (260) to a closed position as shown in FIG. 22B. To drive clamp arm (244) back to the open position, trigger (228) is translated distally away from pistol grip (224) so as to cause distal longitudinal translation of yoke (290) via engagement between pins (292) of yoke (290) and slots (225) of trigger (228). Distal longitudinal translation of yoke (290) causes concurrent distal longitudinal translation of inner tube (234) via the coupling between fork member (293) and coupling feature (267). Distal longitudinal translation of inner tube (234) in turn causes clamp arm (244) to pivot away from blade (260) back into the open position shown in FIG. 22A.

In some versions, one or more resilient members are used to bias clamp arm (244) and/or trigger (228) to the open position shown in FIG. 22A. For instance, as shown in FIGS. 21A and 21B, a spring (236) is positioned within a proximal end of body (222) of handle assembly (220). Spring (236) bears against body (222) and a proximal end of yoke (290) to thereby bias yoke (290) toward the distal longitudinal position. Biasing of yoke (290) toward the distal position causes inner tube (234) to be biased distally and further causes trigger (228) to be biased away from pistol grip (224). Thus, clamp arm (244) is resiliently biased to the open position.

Figure 16:
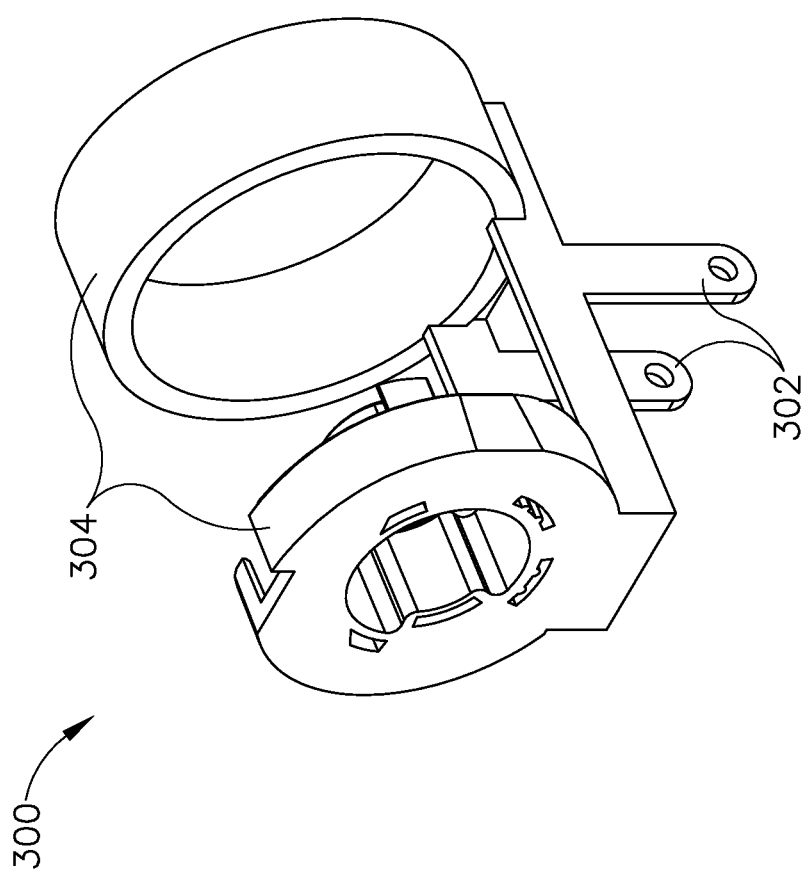
FIG. 16 depicts a perspective view of a sled of the actuation assembly of FIG. 13.

As discussed above, trigger (228) is further operable to pivot toward and away from pistol grip (224) about pins (219) in slots (221). As will be described in more detail below, trigger (228) is coupled with a transducer coupling member (300) such that pivoting trigger (228) toward and away from pistol grip (224) about pins (219) causes longitudinal translation of transducer coupling member (300). As best seen in FIG. 16, transducer coupling member (300) comprises a pair of circular housings (304) and a pair of rods (302) extending downwardly relative to housings (304). As will be discussed in more detail below, transducer assembly (212) is coupled with transducer coupling member (300) via housings (304) such that longitudinal translation of transducer coupling member (300) causes concurrent longitudinal translation of transducer assembly (212) and the remainder of the acoustic drivetrain (i.e., waveguide (202) and blade (260)) along the longitudinal axis of the acoustic drivetrain.

As best seen in FIGS. 13-15, a first link (280) is pivotably coupled to body (222) via a pin (281) extending through a first end (280A) of link (280) such that link (280) operable to rotate about pin (281) within body (222). Pin (281) is fixedly secured with body (222) such that pin (281) is incapable of movement within body (222) and such that first end (280A) of link (280) is incapable of vertical or longitudinal translation. A second end (280B) of link (280) is pivotably coupled to a first end (282A) of a second link (282) via a pin (283) such that link (282) is operable to rotate toward and away from link (280) about pin (283). A second end (282B) of link (282) is slidably and rotatably coupled within elongate slots (227A) via a pin (284) such that second end (282B) of link (282) is longitudinally translatable within oval-shaped slots (227A) via pin (284) between a distal longitudinal position (FIG. 19A) and a proximal longitudinal position (FIG. 19B). It should be understood that pins (281, 284) are positioned along the same horizontal plane and that pin (284) translates along this plane as pin (284) between the distal and proximal positions shown in FIGS. 19A-19B.

Second end (282B) of link (282) is further rotatably coupled with rods (302) of transducer coupling member (300) via pin (284) such that longitudinal translation of second end (282B) of link (282) within elongate slots (227A) causes concurrent longitudinal translation of transducer coupling member (300). Finally, because transducer coupling member (300) is coupled with the acoustic drivetrain via transducer assembly (212), it should be understood that longitudinal translation of second end (282B) of link (282) within elongate slots (227A) causes concurrent longitudinal translation of the acoustic drivetrain.

Pin (283), which couples second end (280B) of link (280) with first end (282A) of link (282), is slidably and rotatably disposed within a slot (229) formed in a proximal portion of trigger (228). The configuration of slot (229) is best seen in FIG. 17. Slot (229) is oriented such that rotation of trigger (228) toward and away from pistol grip (224) about pins (219) in slots (221) causes upward and downward translation of pin (283), respectively. In particular, rotation of trigger (228) away from pistol grip (224) about pins (219) in slots (221) causes downward translation of pin (283); and rotation of trigger (228) toward pistol grip (224) about pins (219) in slots (221) causes upward translation of pin (283). This upward and downward translation of pin (283) will change configuration of links (280, 282) relative to one another between a collapsed configuration (FIG. 19A) and a substantially straight configuration (FIG. 19B). In particular, downward translation of pin (283) moves links (280, 282) from the collapsed configuration to the substantially straight configuration; and upward translation of pin (283) moves links (280, 282) from the substantially straight configuration to the collapsed configuration. Thus, rotation of trigger (228) toward and away from pistol grip (224) about pins (219) in slots (221) changes the configuration of links (280, 282) relative to one another between the collapsed configuration and the substantially straight configuration. In particular, rotation of trigger (228) away from pistol grip (224) about pins (219) in slots (221) moves links (280, 282) from the collapsed configuration to the substantially straight configuration; and rotation of trigger (228) toward pistol grip (224) about pins (219) in slots (221) moves links (280, 282) from the substantially straight configuration to the collapsed configuration.

Figure 19A:
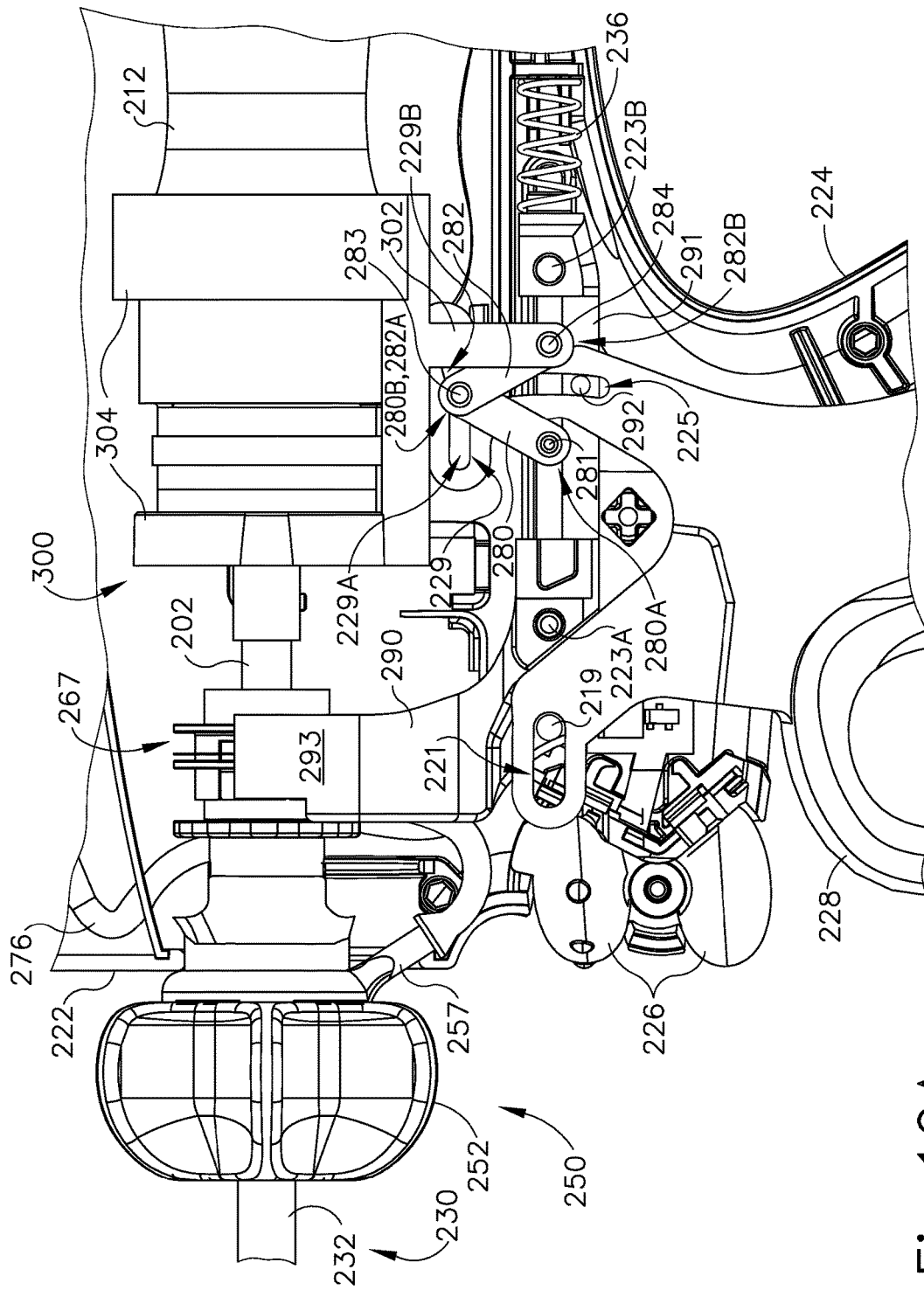
FIG. 19A depicts a side elevational view of the handle assembly of FIG. 8 with a housing shroud removed, with the trigger of FIG. 17 in a first position, and with the sled of FIG. 16 and an acoustic assembly of the instrument of FIG. 9 in a first position.
Figure 19B:
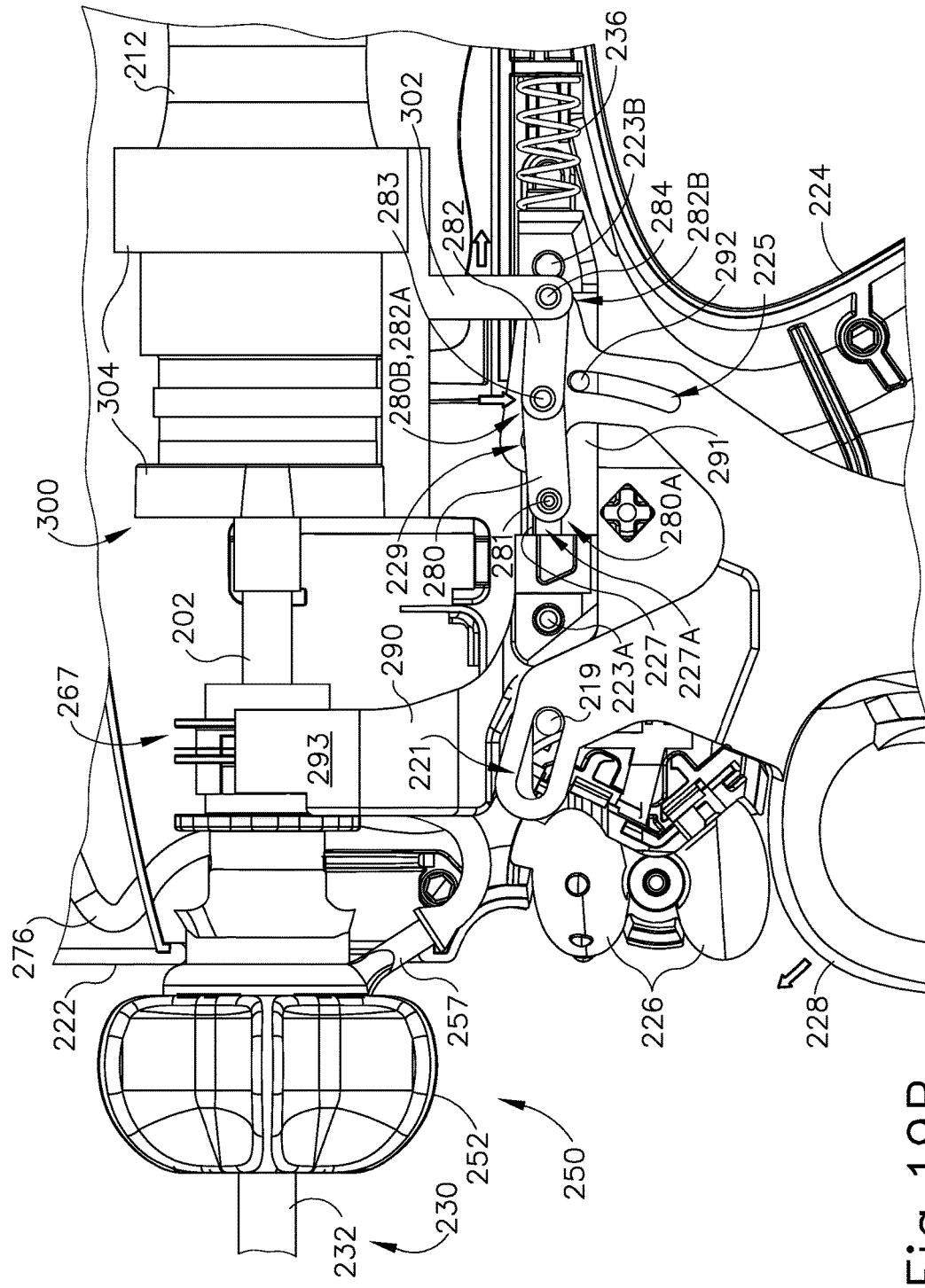
FIG. 19B depicts a side elevational view of the handle assembly of FIG. 8 with a housing shroud removed, with the sled of FIG. 16 and the acoustic assembly of FIG. 19A moved to a second position by rotation of the trigger of FIG. 17 to a second position.

As shown in FIGS. 19A and 19B, as links (280, 282) transition between the collapsed configuration and the substantially straight configuration, a longitudinal distance between first end (280A) of link (280) and second end (282B) of link (282) is increased and decreased. In particular, as links (280, 282) move from the collapsed configuration to the substantially straight configuration, the longitudinal distance between first end (280A) of link (280) and second end (282B) of link (282) is increased; and as links (280, 282) move from the substantially straight configuration to the collapsed configuration, the longitudinal distance between first end (280A) of link (280) and second end (282B) of link (282) is decreased. Because first end (280A) of link (280) is incapable of longitudinal translation, second end (282B) of link (282) must translate longitudinally to accommodate for any increase or decrease in the longitudinal distance between first end (280A) of link (280) and second end (282B) of link (282). In particular, as the longitudinal distance between first end (280A) of link (280) and second end (282B) of link (282) is increased by movement of links (280, 282) from the collapsed configuration to the substantially straight configuration, second end (282B) of link (282) is translated longitudinally proximally. As the longitudinal distance between first end (280A) of link (280) and second end (282B) of link (282) is decreased by movement of links (280, 282) move from the substantially straight configuration to the collapsed configuration, second end (282B) of link (282) is translated longitudinally distally. Thus, because rotation of trigger (228) toward and away from pistol grip (224) changes the configuration of links (280, 282) relative to one another between the collapsed configuration and the substantially straight configuration, it should be understood that rotation of trigger (228) toward and away from pistol grip (224) about pins (219) in slots (221) further causes longitudinal translation of second end (282B) of link (282). In particular, rotation of trigger (228) away from pistol grip (224) about pins (219) in slots (221) causes proximal longitudinal translation of second end (282B) of link (282); and rotation of trigger (228) toward pistol grip (224) about pins (219) in slots (221) causes distal longitudinal translation of second end (282B) of link (282).

Finally, because transducer coupling member (300) is coupled with second end (282B) of link (282), longitudinal translation of second end (282B) of link (282) causes concurrent longitudinal translation of transducer coupling member (300). Because the acoustic drivetrain is coupled with transducer coupling member (300) via transducer assembly (212), longitudinal translation of transducer coupling member (300) causes concurrent longitudinal translation of the acoustic drivetrain, including blade (260). As will be discussed in more detail below, this longitudinal translation of blade (260) causes blade (260) to pass into and out of interior space (253) such that blade (260) contacts the liquid coolant within interior space (253) to thereby cool blade (260). Thus, from the discussion above, it should be understood that rotation of trigger (228) toward and away from pistol grip (224) about pins (219) in slots (221) causes longitudinal translation of blade (260) into and out of interior space (253) to thereby cool blade (260). In particular, rotation of trigger (228) away from pistol grip (224) about pins (219) in slots (221) causes proximal longitudinal translation of blade (260) into interior space (253); and rotation of trigger (228) toward pistol grip (224) about pins (219) in slots (221) causes distal longitudinal translation of blade (260) out of interior space (253). It should be understood from the foregoing that, in some versions, links (280, 282) may cooperate to form a toggle over center assembly that is operable to change the longitudinal position of blade (260) based on the pivotal position of trigger (228) about pins (219) in slots (221). In some such versions, the location of pin (283) may pass over a line extending between pins (281, 284), to assist in effectively locking the acoustic drivetrain in the proximal position.

Figure 20A:
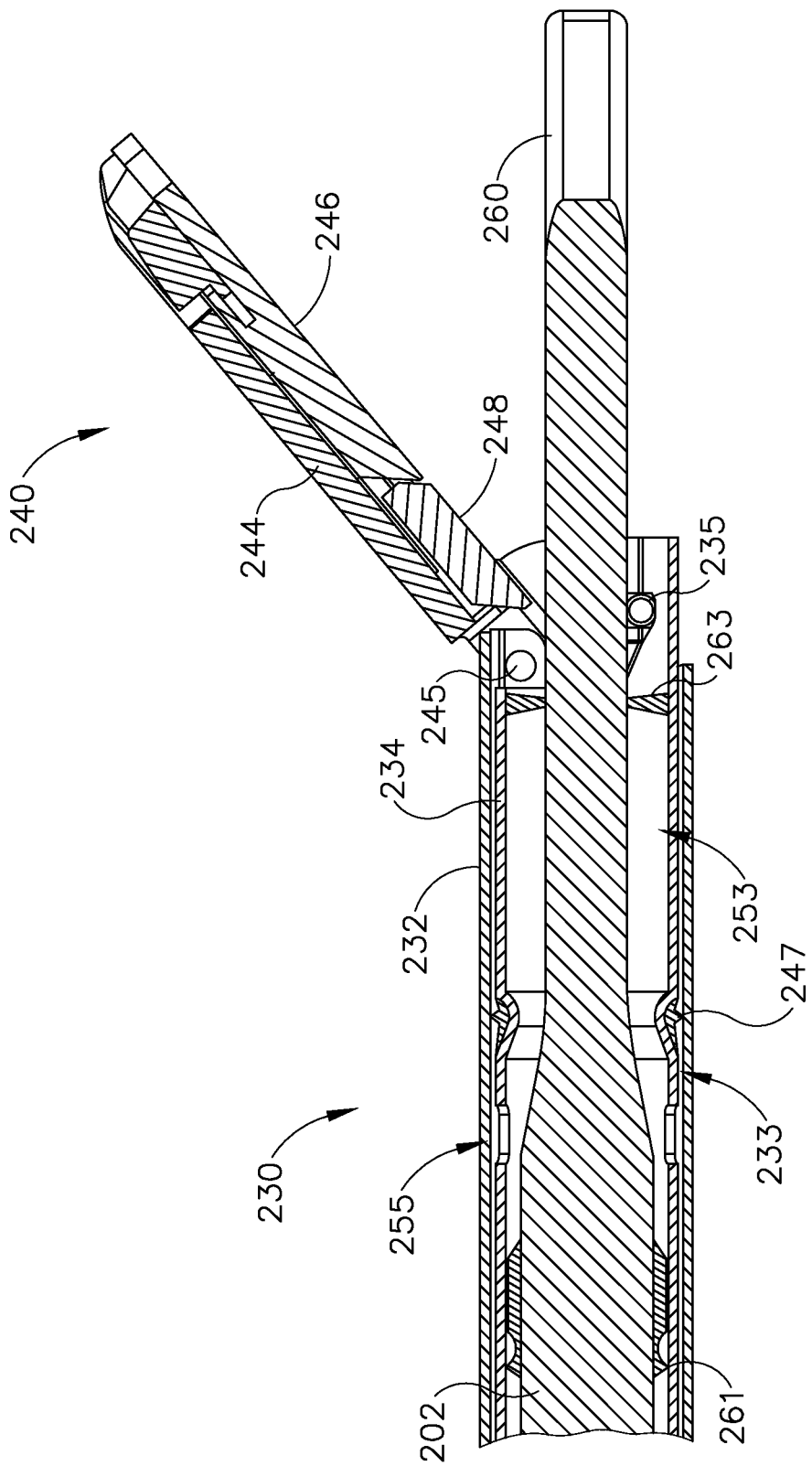
FIG. 20A depicts a cross-sectional side view of the end effector of FIG. 12 in the open position, with the acoustic assembly of FIG. 19A in the first position.
Figure 20B:
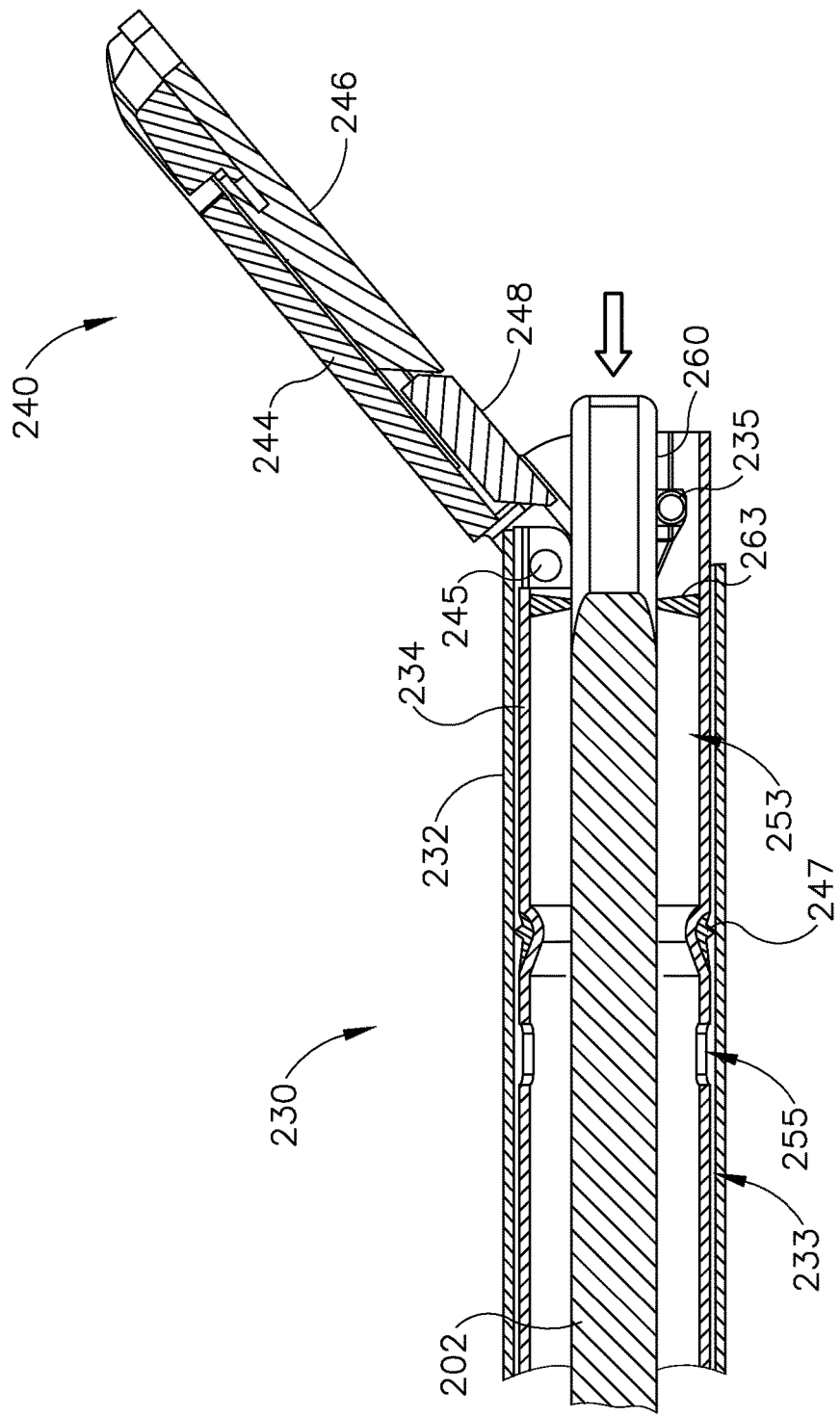
FIG. 20B depicts a cross-sectional side view of the end effector of FIG. 12 in the open position, with the acoustic assembly of FIG. 19A moved to the second position.

FIGS. 19A-20B show another part of the operation of handle assembly (220). FIG. 19A shows trigger (228) in an initial position (the same initial position as shown in FIG. 21A and described above). In this position, links (280, 282) are in the collapsed configuration relative to one another, and transducer coupling member (300) and the acoustic drivetrain are in a distal longitudinal position. In particular, as shown in FIG. 20A, within trigger (228) in this initial position, blade (260) is extended from a distal end of shaft assembly (230). As shown in FIG. 19B, as trigger (228) is rotated away from pistol grip (224) about pins (219) in slots (221), pin (283) is translated downwardly thereby moving links (280, 282) from the collapsed configuration to the to the substantially straight configuration. As discussed above, because first end (280A) of link (280) is incapable of longitudinal translation, as links (280,282) are changed from the collapsed configuration to the substantially straight configuration, second end (282B) of link (282) translates longitudinally proximally to accommodate for the increase in the longitudinal distance between first end (280A) of link (280) and second end (282B) of link (282). As shown in FIG. 19B, because transducer coupling member (300) is coupled with second end (282B) of link (282), as second end (282B) translates longitudinally proximally, transducer coupling member (300) translates longitudinally proximally as well, which in turn causes proximal longitudinal translation of the acoustic drivetrain, including blade (260). In particular, as shown in FIG. 20B, as transducer coupling member (300) translates proximally, blade (260) is drawn proximally within interior space (253) of inner tube (234) so as to contact the liquid coolant to thereby cool blade (260).

To drive blade (260) distally out of interior space (253) of inner tube (234), trigger (228) is rotated toward pistol grip (224) about pins (219) in slots (221) back into the initial position of FIG. 19A to thereby translate pin (283) upwardly thereby moving links (280, 282) from the substantially straight configuration back to the collapsed configuration. Because first end (280A) of link (280) is incapable of longitudinal translation, as linkages (280,282) are changed from the substantially straight configuration to the collapsed configuration, second end (282B) of link (282) translates longitudinally distally to accommodate for the decrease in the longitudinal distance between first end (280A) of link (280) and second end (282B) of link (282). Because transducer coupling member (300) is coupled with second end (282B) of link (282), as second end (282B) translates longitudinally distally, transducer coupling member (300) translates longitudinally distally as well, which in turn causes distal longitudinal translation of the acoustic drivetrain, including blade (260). In particular, as shown in FIG. 20A, as transducer coupling member (300) translates longitudinally distally, blade (260) is driven distally out of interior space (253) of inner tube (234).

As best seen in FIG. 17, slot (229) includes a distal elongate portion (229A) and a proximal elongate portion (229B) oriented at an obtuse angle relative to one another. With trigger (228) in the initial position shown in FIGS. 19A and 21A, pin (283) is positioned between distal elongate portion (229A) and proximal elongate portion (229B), at a vertex of the angle formed by portions (229A, 229B). Also with trigger (228) in the initial position, distal elongate portion (229A) is oriented substantially horizontally such that trigger (228) is able to translate longitudinally proximally relative pin (283) without communicating such translation to pin (283). Thus, as shown in FIGS. 21A and 21B, as trigger (228) is translated proximally from the initial position toward pistol grip (224) to thereby cause rotation of clamp arm (244) into the closed position, this proximal translation of trigger (228) is not communicated to pin (283) and is thus not communicated to the acoustic drivetrain.

In some versions, one or more resilient members are used to bias the acoustic drivetrain to the distal longitudinal position shown in FIG. 20A. For instance, a spring (not shown) may be positioned within body (222) of handle assembly (220) and may be configured to bias pin (283) upwardly. Biasing of pin (283) upwardly causes transducer coupling member (300) to be biased distally and further causes trigger (228) to be biased toward pistol grip (224).

Although instrument (200) is described as utilizing trigger (228) to cause rotation of clamp arm (244) toward and away from blade (260) and to further cause translation of blade (260) into and out of interior space (253), any other appropriate features may be utilized to provide such functionalities as would be apparent to one of ordinary skill in the art. For instance, multiple motors or a single motor and transmission assembly may be utilized to cause rotation of clamp arm (244) toward and away from blade (260) and to further cause translation of blade (260) into and out of interior space (253). Alternatively, one or more translatable knobs may be utilized to cause rotation of clamp arm (244) toward and away from blade (260) and to further cause translation of blade (260) into and out of interior space (253). Other suitable variations will be apparent to those of ordinary skill in the art in view of the teachings herein.

In an exemplary use, instrument (200) may be manipulated to position tissue between clamp arm (244) and blade (260) while clamp arm (244) is in the open position shown in FIG. 22A. The operator may then squeeze trigger (228) toward pistol grip (224) as shown in the transition from FIG. 21A to FIG. 21B, thereby driving clamp arm (244) toward blade (260) as shown in the transition from FIG. 22A to FIG. 22B. This closure of clamp arm (244) will compress the tissue between blade (260) and one or both of clamp pads (246, 248). With the tissue compressed, the operator may actuate one of buttons (226) to ultrasonically activate blade (260), which will sever and seal the tissue that is being compressed against blade (260).

Once the tissue has been adequately severed and sealed, the operator may release their grip on trigger (228), allowing trigger to return back to the position shown in FIG. 21A. This will cause clamp arm (244) to return back to the position shown in FIG. 22A. At this stage (or after one or more subsequent cycles of activating blade (260)), blade (260) may have reached a heated state due to friction encountered as blade (260) was activated. The operator may thus wish to cool blade (260) by quenching blade (260) with liquid coolant. To do so, the operator may drive trigger (228) away from pistol grip (224) as shown in the transition from FIG. 19A to FIG. 19B. This will cause proximal retraction of the acoustic drivetrain, bringing blade (260) into interior space (253) as shown in the transition from FIG. 20A to FIG. 20B. The operator may then communicate liquid coolant from reservoir (270) (e.g., by activating an on-board pump, etc.) to interior space (253) as described above. Blade (260) may thus be cooled by liquid coolant within interior space (253). The operator may maintain this configuration for any suitable duration. Once the operator wishes to advance blade (260) back to the distal position (e.g., for subsequent severing and/or sealing of tissue, etc.), the operator may pivot trigger (228) back toward pistol grip (224) from the position shown in FIG. 19B to the position shown in FIG. 19A. This will drive blade (260) from the position shown in FIG. 20B to the position shown in FIG. 20A. It should be understood that the positioning shown in FIG. 19A is the same as the positioning shown in FIG. 21A; and the positioning shown in FIG. 20A is the same as the positioning shown in FIG. 22A. The above processes may be repeated as many times as desired.

IV. Miscellaneous

As described above, trigger (228) is pivotable through a distal range of motion (relative to a neutral position as shown in FIGS. 19A and 21A) in order to selectively retract blade (260); and through a proximal range of motion (relative to a neutral position as shown in FIGS. 19A and 21A) in order to selectively close end effector (240). In some other versions, trigger (228) moves through three stages in the same direction in order to selectively retract blade (260), advance blade (260), and close end effector (240). For instance, in some other versions, trigger (228) moves proximally toward pistol grip (224) through a first range of motion (relative to a neutral position) in order to selectively retract blade (260). As the operator continues to move trigger (228) proximally toward pistol grip (224), blade (260) advances back to the distal position and clamp arm (244) moves toward blade (260) such that end effector (240) eventually reaches the closed configuration. In other words, a first range of trigger (228) motion provides retraction of blade (260), followed by a second range of trigger (228) motion that provides advancement of blade (260), followed by a third range of motion of trigger (228) that provides closure of end effector (240). Various suitable components and arrangements that may be employed to provide such operability will be apparent to those of ordinary skill in the art in view of the teachings herein.

In addition to or as an alternative to using fluid to reduce heat in a version of instrument (10, 100), one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features are described in U.S. Provisional Patent App. No. 61/908,920, the disclosure of which is incorporated by reference herein; and also in U.S. patent application Ser. No. 14/552,552, entitled "Shielding Features for Ultrasonic Blade of a Surgical Instrument," filed on even date herewith, the disclosure of which is incorporated by reference herein, issued as U.S. Pat. No. 9,993,260 on Jun. 12, 2018; and also in U.S. Patent App. No., entitled "Sleeve Features for Ultrasonic Blade of a Surgical Instrument," filed on even date herewith, the disclosure of which is incorporated by reference herein, issued as U.S. Pat. No. 10,004,528 on Jun. 26, 2018. It should be understood that the teachings herein may be readily combined with the teachings of those references and the various other references cited herein. Other suitable examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement are described in U.S. Provisional Patent App. No. 61/908,920, the disclosure of which is incorporated by reference herein; and also in U.S. patent application Ser. No. 14/552,614, entitled "Ultrasonic Surgical Instrument with Staged Clamping," filed on even date herewith, the disclosure of which is incorporated by reference herein, issued as U.S. Pat. No. 10,004,527. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
    (a) a body;
    (b) a shaft assembly, wherein the shaft assembly extends distally from the body, wherein the shaft assembly defines a longitudinal axis, wherein the shaft assembly comprises:
        (i) an acoustic waveguide, wherein the acoustic waveguide is configured to acoustically couple with an ultrasonic transducer, and
        (ii) an interior space;
    (c) an end effector, wherein the end effector comprises an ultrasonic blade and a clamp arm, wherein the ultrasonic blade is in acoustic communication with the acoustic waveguide, wherein the ultrasonic blade is operable to translate longitudinally relative to the clamp arm such that the ultrasonic blade is configured to move into and out of the interior space of the shaft assembly;
    (d) an actuator; and
    (e) a blade cooling system, wherein the blade cooling system comprises a fluid reservoir coupled with the body, wherein the fluid reservoir is configured to contain liquid coolant, wherein the fluid reservoir is releasably attached to the body such that the fluid reservoir is assembled onto the body, wherein the blade cooling system is configured to provide the liquid coolant to the interior space of the shaft assembly, wherein the actuator is operable to translate the ultrasonic blade into and out of the interior space of the shaft assembly and relative to the clamp arm so as to cause the ultrasonic blade to contact the liquid coolant within the interior space of the shaft assembly to thereby cool the ultrasonic blade.

2. The ultrasonic instrument of claim 1, wherein the actuator comprises a trigger pivotally coupled with the body.

3. The ultrasonic instrument of claim 1, wherein the end effector further comprises a clamp arm operable to move toward and away from the ultrasonic blade.

4. The ultrasonic instrument of claim 3, wherein the actuator is further operable to move the clamp arm toward and away from the ultrasonic blade.

5. The ultrasonic instrument of claim 4, wherein the actuator is movable in a first direction to move the clamp arm toward the ultrasonic blade, wherein the actuator is movable in a second direction to translate the ultrasonic blade into the interior space of the shaft assembly.

6. The ultrasonic instrument of claim 4, wherein the actuator is operable to pivot relative to the body to move the clamp arm toward and away from the ultrasonic blade, wherein the actuator is operable to translate linearly relative to the body to translate the ultrasonic blade into and out of the interior space of the shaft assembly.

7. The ultrasonic instrument of claim 1, wherein the shaft assembly further comprises a rotation knob assembly, wherein the rotation knob assembly is operable to rotate the shaft assembly and the end effector about the longitudinal axis.

8. The ultrasonic instrument of claim 7, further comprising a fluid port located within the rotation knob assembly, wherein the fluid port is configured to provide a fluid coupling between the blade cooling system and the interior space of the shaft assembly.

9. The ultrasonic instrument of claim 1, wherein the blade cooling system comprises a first link and a second link, wherein the first and second links are pivotably coupled with each other at a pin.

10. The ultrasonic instrument of claim 9, wherein the first and second links are configured to move between a collapsed configuration and a substantially straight configuration to thereby translate the ultrasonic blade into and out of the interior space of the shaft assembly.

11. The ultrasonic instrument of claim 10, wherein the actuator is operable to pivot toward and away from the body to thereby move the first linkage and the second linkage between the collapsed configuration and the substantially straight configuration.

12. The ultrasonic instrument of claim 1, wherein the shaft assembly comprises an inner tube and an outer tube, wherein the inner and outer tubes are coaxially disposed about the acoustic waveguide.

13. The ultrasonic instrument of claim 12, wherein the interior space comprises a first interior space region and a second interior space region, wherein the first interior space region is defined between the inner tube and the outer tube, wherein the second interior space region is defined within the inner tube.

14. The ultrasonic instrument of claim 13, wherein a proximal portion of the outer tube comprises at least one lateral aperture, wherein the at least one lateral aperture at the proximal portion of the outer tube provides a fluid passageway to the first interior space region.

15. The ultrasonic instrument of claim 14, further comprising a sealing member interposed between the inner tube and the outer tube, wherein the sealing member is proximal to the at least one lateral aperture at the proximal portion of the outer tube.

16. The ultrasonic instrument of claim 14, wherein a distal portion of the inner tube comprises at least one lateral aperture, wherein the at least one lateral aperture at the distal portion of the inner tube provides a fluid passageway from the first interior space region to the second interior space region.

17. The ultrasonic instrument of claim 16, further comprising a sealing member interposed between the acoustic waveguide and the inner tube, wherein the sealing member is proximal to the at least one lateral aperture at the distal portion of the inner tube.

18. The ultrasonic instrument of claim 1, wherein the blade cooling system comprises a pump configured to provide the liquid coolant to the interior space of the shaft assembly.

19. An apparatus for operating on tissue, the apparatus comprising:
(a) a body;
(b) a shaft assembly, wherein the shaft assembly extends distally from the body, wherein the shaft assembly comprises:
  (i) an acoustic waveguide, wherein the acoustic waveguide is configured to acoustically couple with an ultrasonic transducer,
  (ii) an interior space,
  (iii) an interior surface, and
  (iv) a sealing member fixedly secured to the interior surface of the shaft assembly and disposed within the interior space;
(c) a blade cooling system, wherein the blade cooling system is configured to provide liquid coolant to the interior space of the shaft assembly;
(d) an end effector, wherein the end effector comprises:
  (i) an ultrasonic blade in acoustic communication with the acoustic waveguide, and
  (ii) a clamp arm, wherein the clamp arm is movable toward and away from the ultrasonic blade; and
(e) an actuator, wherein the actuator is movable through a first range of motion to relative to the body thereby move the clamp arm toward the ultrasonic blade, wherein the actuator is further movable through a second range of motion relative to the body to thereby move the ultrasonic blade into the interior space of the shaft assembly to thereby cause the ultrasonic blade to contact the liquid coolant within the interior space of the shaft assembly, wherein the acoustic waveguide is configured to move within the interior space and slidably engage the sealing member in response to movement of the ultrasonic blade.

20. An apparatus for operating on tissue, the apparatus comprising:
(a) a body, wherein the body includes an engagement surface;
(b) a shaft assembly, wherein the shaft assembly extends distally from the body, wherein the shaft assembly defines a longitudinal axis, wherein the shaft assembly comprises:
  (i) a tube,
  (ii) an acoustic waveguide positioned within the tube, wherein the acoustic waveguide is configured to acoustically couple with an ultrasonic transducer, and
  (iii) an interior space;
(c) an end effector, wherein the end effector comprises an ultrasonic blade in acoustic communication with the acoustic waveguide and a clamp arm, wherein the ultrasonic blade and the acoustic waveguide are operable to retract proximally relative to the clamp arm and relative to the tube to thereby position the ultrasonic blade in the interior space of the shaft assembly and proximal to the clamp arm; and
(d) a blade cooling system, wherein the blade cooling system comprises a fluid reservoir coupled with the body, wherein the fluid reservoir is configured to contain liquid coolant, wherein the fluid reservoir is configured to selectively attach to the engagement surface of the body, wherein the blade cooling system is configured to provide the liquid coolant to the interior space of the shaft assembly to thereby cool the ultrasonic blade.

* * * * *